(12) United States Patent
Belalcazar et al.

(10) Patent No.: US 7,447,543 B2
(45) Date of Patent: Nov. 4, 2008

(54) PATHOLOGY ASSESSMENT WITH IMPEDANCE MEASUREMENTS USING CONVERGENT BIOELECTRIC LEAD FIELDS

(75) Inventors: Andres Belalcazar, St. Paul, MN (US); Robert Patterson, Minneapolis, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 450 days.

(21) Appl. No.: 11/058,123

(22) Filed: Feb. 15, 2005

(65) Prior Publication Data
US 2006/0184060 A1 Aug. 17, 2006

(51) Int. Cl.
*A61B 5/053* (2006.01)
(52) U.S. Cl. ............................. 600/547; 600/301
(58) Field of Classification Search ................ 600/547, 600/301, 506, 483, 484
See application file for complete search history.

(56) References Cited

U.S. PATENT DOCUMENTS

| | | | |
|---|---|---|---|
| 3,340,867 A | 9/1967 | Kubicek et al. | |
| 4,540,002 A * | 9/1985 | Atlas .......................... | 600/547 |
| 4,905,705 A | 3/1990 | Kizakevich et al. | |
| 4,932,408 A | 6/1990 | Schaldach | |
| 5,154,170 A | 10/1992 | Bennett et al. | |
| 5,199,428 A | 4/1993 | Obel et al. | |
| 5,246,008 A | 9/1993 | Mueller | |
| 5,282,840 A | 2/1994 | Hudrlik | |
| 5,358,519 A | 10/1994 | Grandjean | |
| 5,365,426 A | 11/1994 | Siegel et al. | |
| 5,438,987 A | 8/1995 | Thacker et al. | |
| 5,454,377 A | 10/1995 | Dzwonczyk et al. | |
| 5,501,702 A | 3/1996 | Plicchi et al. | |
| 5,556,421 A | 9/1996 | Prutchi et al. | |
| 5,807,272 A | 9/1998 | Kun et al. | |
| 5,814,076 A | 9/1998 | Brownlee | |
| 5,824,029 A | 10/1998 | Weijand et al. | |
| 5,876,353 A | 3/1999 | Riff | |
| 5,931,858 A | 8/1999 | Kadhiresan et al. | |
| 5,957,861 A | 9/1999 | Combs et al. | |
| 5,974,340 A | 10/1999 | Kadhiresan | |

(Continued)

OTHER PUBLICATIONS

Bocchiardo et al., "Biventricular Pacing Optimization Using Impedance Feasibility Study," *Europace Supplements*, 2002, 3:A39, Abstract No. 54/3.

(Continued)

*Primary Examiner*—Kennedy J Schaetzle
(74) *Attorney, Agent, or Firm*—Fish & Richardson P.C.

(57) ABSTRACT

A method and apparatus for measuring impedance for pathology assessment in a living being using convergent bioelectric lead fields is disclosed, including injecting a current between first and second electrodes implanted in a body of a living being, where the first and second electrodes define a first electric lead field oriented between the first and second electrodes. A potential difference is measured between third and fourth electrodes implanted in the body, where the potential difference results from the current injected between the first and second electrodes. The third and fourth electrodes define a second electric lead field oriented between the third and fourth electrodes. The first and second electric lead fields converge near an assessment site within the body, but are substantially separated otherwise. An impedance value is calculated based on the potential difference and the current injection, and is used to assess a pathology near the assessment site.

39 Claims, 13 Drawing Sheets

U.S. PATENT DOCUMENTS

| | | | |
|---|---|---|---|
| 6,021,350 | A | 2/2000 | Mathson |
| 6,038,469 | A | 3/2000 | Karlsson et al. |
| 6,070,100 | A | 5/2000 | Bakels et al. |
| 6,128,526 | A | 10/2000 | Stadler et al. |
| 6,161,042 | A | 12/2000 | Hartley et al. |
| 6,223,079 | B1 | 4/2001 | Bakels et al. |
| 6,233,486 | B1 | 5/2001 | Ekwall et al. |
| 6,256,538 | B1 | 7/2001 | Ekwall |
| 6,264,606 | B1 | 7/2001 | Ekwall et al. |
| 6,269,264 | B1 | 7/2001 | Weyant et al. |
| 6,277,078 | B1 | 8/2001 | Porat et al. |
| 6,278,894 | B1 | 8/2001 | Salo et al. |
| 6,360,123 | B1 | 3/2002 | Kimchi et al. |
| 6,381,493 | B1 | 4/2002 | Stadler et al. |
| 6,424,860 | B1 | 7/2002 | Karlsson et al. |
| 6,434,408 | B1 | 8/2002 | Mulligan et al. |
| 6,454,719 | B1 | 9/2002 | Greenhut |
| 6,473,640 | B1 | 10/2002 | Erlebacher |
| 6,512,949 | B1 | 1/2003 | Combs et al. |
| 6,539,261 | B2 | 3/2003 | Dal Molin |
| 6,564,099 | B2 | 5/2003 | Prutchi et al. |
| 6,595,927 | B2 | 7/2003 | Pitts-Crick et al. |
| 6,604,000 | B2 | 8/2003 | Lu |
| 6,788,972 | B2 | 9/2004 | Prutchi et al. |
| 2001/0020138 | A1 | 9/2001 | Ishigooka et al. |
| 2002/0002389 | A1 | 1/2002 | Bradley et al. |
| 2002/0072686 | A1* | 6/2002 | Hoey et al. .............. 600/547 |
| 2002/0115939 | A1 | 8/2002 | Mulligan et al. |
| 2002/0123674 | A1 | 9/2002 | Plicchi et al. |
| 2002/0143368 | A1 | 10/2002 | Bakels et al. |
| 2002/0161310 | A1 | 10/2002 | Daum |
| 2003/0023184 | A1 | 1/2003 | Pitts-Crick et al. |
| 2003/0028221 | A1 | 2/2003 | Zhu et al. |
| 2003/0045805 | A1 | 3/2003 | Sheldon et al. |
| 2003/0078619 | A1 | 4/2003 | Bonnet et al. |
| 2003/0093125 | A1 | 5/2003 | Zhu et al. |
| 2003/0149368 | A1 | 8/2003 | Hennemann et al. |
| 2003/0204209 | A1 | 10/2003 | Burnes et al. |
| 2004/0087870 | A1 | 5/2004 | Jarverud |
| 2004/0215097 | A1 | 10/2004 | Wang |

OTHER PUBLICATIONS

Bronzino (ed.), "Chapter 73—Bioelectric Impedance Measurements," *The Biomedical Engineering Handbook*, Second Edition, 2000, 1:73-1-73-8.

Cole et al., "Correlation of Impedance Minute Ventilation with Measured Minute Ventilation in a Rate Responsive Pacemaker," *PACE*, 2001, 24:989-993.

Duru et al., "Rate Responsive Pacing Using Transthoracic Impedance Minute Ventilation Sensors: A Multicenter Study on Calibration Stability," *PACE*, 2002, 25(12):1679-1684.

Gersing et al., "Measurement of Electrical Impedance in Organs—Fundamentals and Methodology," *Biomed. Technik*, 1991, 36(4):70-77.

Hauck, "A Minute Ventilation Sensor Derived from Intra-Thoracic Electric Impedance as a Cardiac Pacemaker Rate Modulator," A Thesis Submitted to the Faculty of the Graduate School of the University of Minnesota, Department of Electrical Engineering, Jun. 1993, 148 pgs.

Malmivuo and Plonsey, *Bioelectromagnetism: Principles and Applications of Bioelectric and Biomagnetic Fields*, 1995, sections 11.6.2 and 25.2.1, beginning at pp. 202 and 405, respectively.

Nappholtz et al., "Electrode Configurations for a Respiratory Impedance Measurement Suitable for Rate Responsive Pacing," *PACE*, 1986, Part II, vol. 9, pp. 960-964.

Patterson, "Possible technique to measure ventricular volume using electrical impedance measurements with an oesophageal electrode," *Med. & Biol. Eng. & Comput.*, 1987, 25:677-679.

Plicchi et al., "Monitoring Intrapulmonary Bioelectric Impedance During Active Volume Overloading," *Europace Supplements*, 2002, 3:A39, Abstract No. 54/6.

Salazar et al., "Transmural Versus Nontransmural *In Situ* Electrical Impedance Spectrum for Healthy, Ischemic, and Healed Myocardium," *IEEE Transactions on Biomedical Engineering*, 2004, 51(8):1421-1427.

Schwartzman et al., "Electrical Impedance Properties of Normal and Chronically Infarcted Left Ventricular Myocardium," *Journal of Interventional Cardiac Electrophysiology*, 1999, 3:213-224.

Van De Water et al., "Monitoring the Chest with Impedance," *Chest*, 1973, 64(5):597-603.

Wang et al., "Feasibility of Predicting CHF Hospitalization Using Pacemaker-Based Impedance Sensor in CHF Patients," *J. Cardiac Failure*, 2002, 8(4 Suppl.):S81, Abstract No. 297.

Wang et al., "Feasibility of Monitoring Thoracic Congestion with Impedance Measured from an ICD Lead System in a Chronic Heart Failure Dog Model," *PACE*, NASPE Abstracts, 2000, Part II, vol. 23, No. 4, p. 612, Abstract No. 237.

Yu et al., "Early Warning of CHF Hospitalization by Intra-Thoracic Impedance Measurement in CHF Patients with Pacemakers," *PACE*, NASPE Abstracts, 2002, Part II, vol. 25, No. 4, p. 527, Abstract No. 19.

"Single-chamber cardiac pacing with two forms of respiration-controlled rate-responsive pacemaker" by Lau et al., *Chest, Official publication of the American College of Chest Physicians*, pp. 352-358, 1989.

* cited by examiner

100

| 4TH ELECTRODE, LV SP. | BASELINE OHMS | SEVERE EDEMA OHMS | % CHANGE |
|---|---|---|---|
| IMPEDANCE RESPONSES WITH LV TETRAPOLAR SYSTEMS | | | |
| 102a { BRACHIO RING, 15 MM | 34.62 | 22.61 | 34.69 |
| 102b { BRACHIO RING, 25 MM | 14.85 | 8.81 | 40.67 |
| 102c { SVC HIGH, 25 MM | 10.27 | 5.64 | 45.08 |
| 102d { SVC LOW, 25 MM | 7.29 | 3.76 | 48.50 |
| 102e { RA RING, 15 MM | 25.49 | 16.71 | 34.44 |
| 102f { RA RING, 25 MM | 5.43 | 2.63 | 51.60 |

FIG. 5

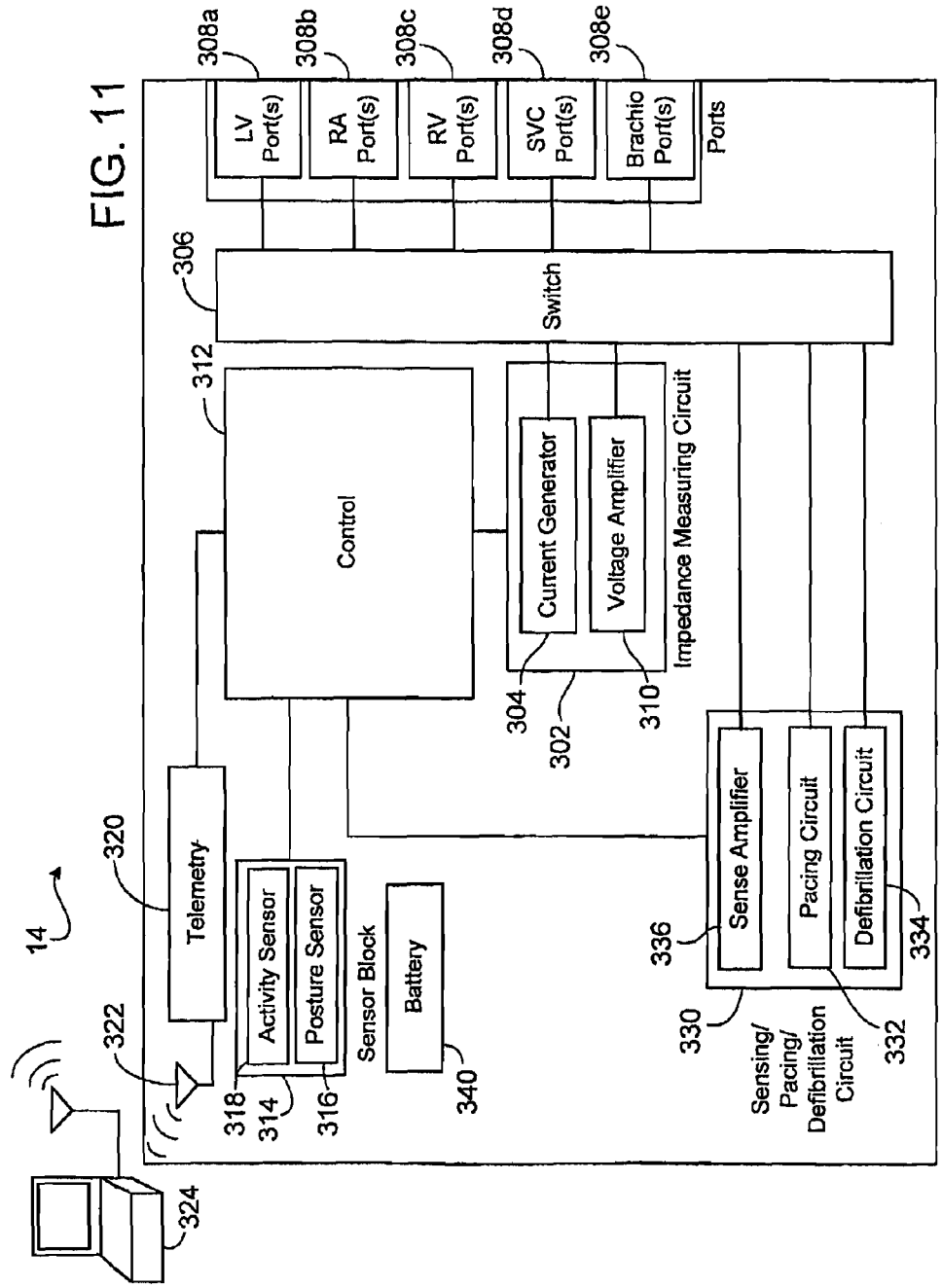

| Impedance Sensitivity Coefficients: Tripolar vs Convergent Tetrapolar | | | | | | | |
|---|---|---|---|---|---|---|---|
| Tissue | LVCV tri | RV coil trl | Brachio 15 | Brachio 25 | SVC | RA 15 | RA 25 |
| VESSELS | | | | | | | |
| superior vena cava | 0.0003 | 0.0006 | 0.0012 | 0.0030 | 0.0089 | -0.0062 | -0.0306 |
| inferior vena cava | 0.0001 | 0.0003 | 0.0003 | 0.0006 | 0.0013 | 0.0003 | 0.0013 |
| pulmonary trunk | 0.0034 | 0.0081 | 0.0103 | 0.0248 | 0.0329 | -0.0002 | -0.0029 |
| ascending aorta | 0.0007 | 0.0019 | 0.0030 | 0.0073 | 0.0241 | -0.0040 | -0.0201 |
| aortic arch | 0.0016 | 0.0028 | 0.0072 | 0.0181 | -0.0144 | -0.0023 | -0.0107 |
| descending aorta | 0.0011 | 0.0015 | 0.0023 | 0.0069 | 0.0077 | 0.0005 | 0.0055 |
| brachicephisubcl vessels | 0.0054 | 0.0083 | -0.0011 | -0.0021 | -0.0240 | -0.0026 | -0.0114 |
| azygous vein | 0.0001 | 0.0002 | 0.0002 | 0.0006 | -0.0012 | -0.0001 | -0.0004 |
| all other vessels | 0.0030 | 0.0059 | 0.0059 | 0.0137 | 0.0263 | 0.0107 | 0.0504 |
| HEART | | | | | | | |
| RA blood | 0.0007 | 0.0050 | 0.0019 | 0.0042 | 0.0142 | 0.0131 | 0.0629 |
| RV blood | 0.0024 | 0.0517 | 0.0065 | 0.0116 | 0.0329 | 0.0123 | 0.0486 |
| LA blood | 0.0038 | 0.0026 | 0.0089 | 0.0256 | 0.0642 | 0.0148 | 0.0816 |
| LV blood | 0.0620 | 0.0164 | 0.1225 | 0.0853 | 0.1644 | 0.1789 | 0.2466 |
| RV anterior wall, apex | 0.0003 | 0.0368 | 0.0007 | 0.0011 | 0.0028 | 0.0012 | 0.0040 |
| LV lateral wall | 0.1258 | 0.0069 | 0.2514 | -0.0806 | -0.1731 | 0.3394 | -0.1950 |
| all other heart muscle | 0.0171 | 0.0531 | 0.0339 | 0.0638 | 0.1823 | 0.0601 | 0.2325 |
| epicardial fat | 0.0605 | 0.0440 | 0.1075 | 0.1077 | 0.1453 | 0.1069 | 0.0993 |
| LUNGS | | | | | | | |
| right lung | 0.0016 | 0.0044 | 0.0047 | 0.0111 | -0.0046 | -0.0064 | -0.0323 |
| left lung | 0.1834 | 0.0794 | 0.2548 | 0.3196 | 0.3941 | 0.2493 | 0.4175 |
| pulmonary vessels | 0.0129 | 0.0112 | 0.0175 | 0.0452 | 0.0476 | 0.0076 | 0.0421 |
| OTHERS | | | | | | | |
| muscle near generator | 0.1888 | 0.2199 | 0.0109 | 0.0217 | 0.0082 | 0.0024 | -0.0006 |
| fat near generator | 0.1048 | 0.1212 | -0.0003 | -0.0019 | 0.0001 | 0.0003 | -0.0005 |
| all other muscle | 0.1107 | 0.1534 | 0.0850 | 0.1639 | -0.0110 | -0.0096 | -0.0400 |
| all other fat | 0.0832 | 0.1236 | 0.0703 | 0.1409 | 0.0440 | 0.0261 | 0.0382 |
| spinal bord | 0.0003 | 0.0004 | 0.0008 | 0.0021 | 0.0012 | 0.0000 | 0.0002 |
| bone, cartilage | 0.0195 | 0.0245 | 0.0024 | 0.0054 | -0.0057 | -0.0012 | -0.0068 |
| liver | 0.0007 | 0.0064 | 0.0026 | 0.0053 | 0.0126 | 0.0010 | 0.0020 |
| spleen, kidneys | 0.0003 | 0.0011 | 0.0004 | 0.0008 | 0.0009 | 0.0002 | 0.0003 |
| stomach | 0.0003 | 0.0022 | 0.0006 | 0.0010 | 0.0021 | 0.0007 | 0.0026 |
| esophagus | 0.0005 | 0.0008 | 0.0016 | 0.0041 | 0.0008 | -0.0002 | -0.0004 |
| diaphragm | 0.0037 | 0.0052 | 0.0062 | 0.0088 | 0.0151 | 0.0069 | 0.0160 |

FIG. 12

PATHOLOGY ASSESSMENT WITH IMPEDANCE MEASUREMENTS USING CONVERGENT BIOELECTRIC LEAD FIELDS

TECHNICAL FIELD

This disclosure relates to impedance monitoring in a living being, and using impedance measurements to detect and assess medical pathologies in the living being.

BACKGROUND

Myocardial ischemia is a serious medical condition resulting from inadequate blood supply to the myocardium, a muscle of the heart that alternately contracts to permit the heart's ventricular chambers to pump blood, and then relaxes to permit the heart's chambers to receive blood. Ischemia is characterized by abnormally low myocardial blood perfusion; that is, abnormally low blood flow to myocardial tissue. An ischemic event can be triggered by a rupture of a plaque in a coronary artery, an event that may generate a clot causing the artery to become occluded and prevent oxygenated blood from reaching myocardial tissue. When this occurs, a patient may experience chest pain, but may discount the sensation as an aberration or assume that the pain is related to another condition, such as arthritis, for example. Other times, the patient may not feel any pain. Within seconds of an ischemic event, myocardium contractility can become impaired as the myocardial tissue becomes starved of oxygen, resulting from the lack of blood flow due to the occlusion. Within fifteen to twenty minutes of the event, heart damage can occur if the blockage is not removed, and the longer the heart muscle is deprived of oxygen, the greater the risk of irreversible muscle damage, which may occur after a few hours. Prompt detection of an ischemic event is therefore desirable, and may allow timely therapeutic interventions, such as various thrombolytic or angioplastic therapies designed to clear the occluding material and restore free blood flow to the myocardial tissue.

One known method of detecting ischemia is to obtain an electrocardiogram (ECG) of a patient's coronary electrical activity, and analyze the S-T segment of the ECG for deviations. The S-T segment is the portion of the ECG signal between the S wave and the T wave, and is known to exhibit variations following an ischemic event. Detecting an S-T segment deviation may indicate ischemia. An ECG may be obtained using twelve leads placed in various locations externally on the skin of the patient to sense coronary electrical activity in a manner known to those skilled in the art. Another method of obtaining an ECG uses electrodes attached to an implanted medical device, such as a pacemaker or defibrillator, implanted in a chest region of a patient to sense cardiac electrical activity. The S-T segment of this ECG can then be analyzed for deviations in the manner described above.

Similarly, pulmonary edema is also a serious medical condition. Pulmonary edema is characterized by an excess accumulation of fluid within a patient's lungs, and can be an indicator of cardiac-related diseases, such as heart failure. It is possible to detect fluid in the lungs by making an electrical impedance measurement across the lungs. The more fluid present in the lungs, the lower the impedance. One known way of making such an electrical impedance measurement is to use an implanted medical device such as a pacemaker or defibrillator. An electrical impedance measurement is conventionally made between right ventricular chamber electrodes connected by a lead to the implanted medical device, and another electrode at the implanted medical device itself. As such, the impedance measurement samples thoracic tissues, including the lungs.

U.S. patent application Ser. No. 10/303,305, filed on Nov. 25, 2002, by Andres Belalcazar and Robert Patterson (the present inventors), and Rebecca Shult, describes another way of measuring lung impedance using an implantable medical device to make an electrical impedance measurement between an electrode positioned epicardially over the left ventricular wall of the heart and connected to the implantable medical device, and another electrode at the implantable medical device itself. The impedance is measured by applying an electrical stimulus current to the implanted electrodes and measuring the resulting voltage using other implanted electrodes, and then calculating the ratio of voltage to current. It is also possible to detect fluid changes in the lungs by making an electrical impedance measurement using only external electrodes attached to the skin.

SUMMARY

Generally, the invention provides improved techniques for detecting and assessing medical pathologies within a living being by measuring electrical impedance across one or more thoracic organs or tissues.

In one general aspect, the invention features a method of measuring impedance for pathology assessment in a living being. The method includes injecting a current between first and second electrodes implanted in a body of a living being, where the first and second electrodes define a first electric lead field in the body, and the first electric lead field is oriented between the first and second electrodes. The method also includes measuring a potential difference between third and fourth electrodes implanted in the body, where the potential difference results from the current injected between the first and second electrodes. The third and fourth electrodes define a second electric lead field in the body, and the second electric lead field is oriented between the third and fourth electrodes. The first and second electric lead fields converge near an assessment site within the body, but are substantially separated otherwise. The method further includes calculating an impedance value based on the potential difference and the current injection, and using the impedance value to assess a pathology near the assessment site.

In another general aspect, the invention features a method of measuring impedance phase angle for pathology assessment in a living being. The method includes injecting a current between first and second electrodes implanted in a body of a living being, where the first and second electrodes define a first electric lead field in the body, and the first electric lead field is oriented between the first and second electrodes. The method also includes measuring a potential difference between third and fourth electrodes implanted in the body, where the potential difference results from the current injected between the first and second electrodes. The third and fourth electrodes define a second electric lead field in the body, and the second electric lead field is oriented between the third and fourth electrodes. The first and second electric lead fields converge near an assessment site within the body, but are substantially separated otherwise. The method further includes calculating an impedance phase angle value based on the potential difference and the current injection, and using the impedance phase angle value to assess a pathology near the assessment site.

In another aspect, the invention features an implantable medical device for measuring impedance for pathology assessment in a living being. The implantable medical device includes a pulse generator to inject a current between first and second electrodes implanted in a body of a living being, where the first and second electrodes define a first electric lead field in the body, and the first electric lead field is oriented between the first and second electrodes. The implantable medical device also includes a voltage measurement circuit to measure a potential difference between third and fourth electrodes implanted in the body, where the potential difference results from the current injected between the first and second electrodes. The third and fourth electrodes define a second electric lead field in the body, with the second electric lead field oriented between the third and fourth electrodes. The first and second electric lead fields converge near an assessment site within the body, but are substantially separated otherwise. The implantable medical device further includes a processing unit to calculate an impedance value based on the potential difference and the current injection, and to use the impedance value to assess a pathology near the assessment site.

Implementations of the method and the apparatus may include one or more of the following. The assessment site may not be within a heart chamber. The assessment site may be a left lung or a left ventricular wall of a heart, and the pathology may be pulmonary edema, myocardial ischemia, or left ventricular hypertrophy. The second and fourth electrodes may be separated by about fifteen millimeters or by about twenty-five millimeters. The first and third electrodes may be separated by at least about four centimeters, or by at least about ten centimeters. The second and fourth electrodes may be positioned near a left ventricle of a heart. The first electrode may be positioned in a pectoral region or in a right ventricle of the heart, and the third electrode may be positioned in a right atrium of the heart, near a brachiocepahlic vein, or in a superior vena cava. An alarm may be triggered in response to the pathology assessment, and the impedance value may be stored for later reference. The impedance value may be compared to a threshold value or transmitted to a monitoring station. The processing unit may trigger an alarm in response to the pathology assessment and a transceiver may transmit the impedance value to a monitoring station.

In another aspect, a second current may be injected between the first and second electrodes, a second potential difference may be measured between the third and fourth electrodes, a second impedance value may be calculated based on the second potential difference and the second current injection, and the first and second impedance values may be used to assess the pathology near the assessment site. The first and second currents may be alternating currents of different frequencies, and the second potential difference may result from the second current injected between the first and second electrodes. The first current may have a frequency of about one kilohertz and the second current may have a frequency of about five hundred kilohertz. The pathology may be classified based on the first and second impedance values, and effects of two or more pathologies may be discriminated based on the first and second impedance values. The current may be a composite signal comprising two or more frequencies, and frequency components corresponding to the two or more frequencies may be extracted from the potential difference, which may be a voltage signal. Similarly, an impedance phase angle value may be calculated based on the second potential difference and the second current injection, and the first and second impedance phase angle values may be used to assess or classify the pathology near the assessment site, or discriminate the effects of two or more pathologies.

Advantages of the invention may include one or more of the following. Greater levels of impedance sensitivity and specificity are possible using aspects of the invention because sensitivity is concentrated primarily near the region of interest. Moreover, sensitivity is reduced in regions of non-interest. This sensitivity concentration near the region of interest, combined with reduced sensitivity to regions of non-interest, permits better assessment and detection of pathologies near the region of interest, because measured impedance changes are more likely to be due to resistivity changes from organs, tissue or fluids within the region of interest, rather than to resistivity changes from organs, tissue or fluids outside of the region of interest. As such, more accurate early detection and assessment of pathologies may be possible, and false alarms triggered by measured impedance changes resulting from resistivity changes in regions of non-interest may be avoided.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 is a table of simulation results.

FIG. 11 is a schematic block diagram of an implantable medical device for use with any of the systems of FIGS. 1-4 and 7-9.

FIG. 12 is a table of simulation results.

Like reference symbols in the various drawings indicate like elements.

DETAILED DESCRIPTION

Figure 1:
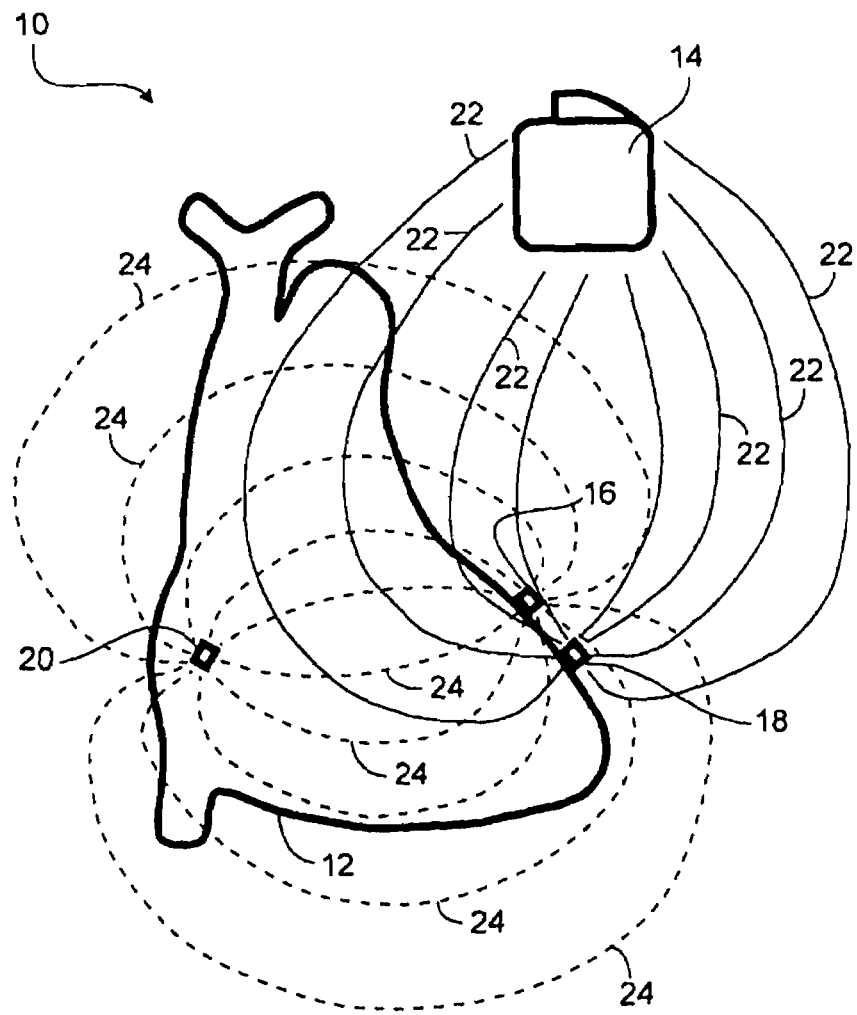
FIG. 1 is a perspective diagram of a convergent bioelectric lead field system.

FIG. 1 shows a system 10 that includes a heart 12 and an implantable medical device (IMD) 14, which may be implanted in a chest region of a patient. IMD 14 includes a pulse generator for generating electrical current and a voltage sense circuit for sensing potential differences (i.e., voltages). IMD 14 may be a pacemaker, a defibrillator, a combination thereof, or any other type of implantable medical device capable of delivering current stimulation to thoracic tissue and measuring voltages. The IMD 14 may include an electrode, conventionally known as a "can" electrode, on an exterior surface of the device 14. In this illustrative system 10, three additional electrodes 16, 18, 20 are shown, and may be attached to leads (not shown) that connect to IMD 14. The electrodes 16, 18, 20 may be electrically connected to IMD 14 through conductors that run through the leads, facilitating electrical current injections from the pulse generator between any two of the four electrodes 16, 18, 20, or the can electrode. Similarly, the voltage sense circuit may sense a voltage between any two of the four electrodes 16, 18, 20, or the can electrode. An impedance computation module within the IMD 14 may then calculate an impedance by taking a ratio of the measured voltage to the injected current, in accordance with Ohm's law. Because four electrodes are utilized in such an impedance measurement, the electrode configuration shown in system 10 may be referred to as a tetrapolar configuration. In the tetrapolar configuration depicted in FIG. 1, electrodes 16 and 18 are positioned over a left ventricle of the heart 12, while electrode 20 is positioned in a right atrium of the heart 12. Electrode 16 may be referred to as a proximal left ventricular electrode and electrode 18 may be referred to as a distal left ventricular electrode because of proximal and distal positions they might assume on a left ventricular lead (not shown in FIG. 1).

Because the human body includes a number of thoracic organs, tissues, and fluids, measurements of thoracic impedance include contributions from each of the various organs, tissues, and fluids. For example, resistivities of the heart muscle, lungs, pectoral muscle, pectoral fat, liver, kidneys, spleen, stomach, skeletal muscle, bone, cartilage, blood and other tissues and fluids each contribute to a measurement of thoracic impedance. As such, changes in measured thoracic impedance can be caused by changes in the resistivities of these and other organs or tissues.

When measuring impedance to detect or assess pathologies, such as pulmonary edema or myocardial ischemia, it is desirable to measure impedances using electrode configurations that are highly sensitive to a region or regions of interest, such as the lungs or the myocardium, respectively. High sensitivity to the region or regions of interest permits sensitive detection of resistivity changes in the organ or tissue of interest, because the change in resistivity of the organ or tissue of interest will have a correspondingly large impact on the measured impedance. Thus, impedance changes may indicate the presence of the pathological condition. Moreover, it is also desirable that such configurations provide relatively low sensitivity to all organs, tissues, and fluids not in the region of interest, such that resistivity changes in these organs, tissues, and fluids have a correspondingly small impact on the measured impedance.

Referring again to FIG. 1, the system shows two bioelectric lead fields 22, 24. A first bioelectric lead field 22 originates from the can electrode and terminates at the distal left ventricular electrode 18. A second bioelectric lead field 24 (represented by dashed lines in FIG. 1) originates from the right atrial electrode 20 and terminates at the proximal left ventricular electrode 16. As seen in FIG. 1, the first bioelectric lead field 22 is most dense near the distal left ventricular electrode 18 and near the can electrode, as indicated by the closer spacing of the bioelectric field lines in these areas. Similarly, the second bioelectric lead field 24 is most dense near the proximal left ventricular electrode 16 and the right atrial electrode 20.

The first and second bioelectric lead fields 22, 24 may be referred to as convergent bioelectric lead fields, because they originate at locations relatively distant from one another (here, at a left pectoral region and the right atrium, respectively), but terminate in close proximity to one another (here, near the left ventricle). As such, the converging bioelectric lead field lines merge with a high density only in a region of interest. Sensitivity is concentrated in this region of interest—the lateral left ventricle and its neighboring left-lung region in this example. This high density of merged bioelectric field lines near the impedance measurement region of interest, and lack of concentrated merged lead fields in other regions, facilitates impedance measurements that are highly sensitive and specific to resistivity changes in the region of interest, as will be described more fully below. This may be contrasted with impedance measurement configurations, such as conventional bipolar and tripolar electrode configurations, as well as conventional tetrapolar electrode configurations, where the corresponding bioelectric lead fields densely merge in two regions, resulting in impedance sensitivity not only to the region of interest, but also to a region of non-interest (corresponding to the other region of densely merged fields).

The first bioelectric lead field 22 (which may be associated with stimulation electrodes, for example) may be defined as the field of current density vectors resulting from a unity current injection between the can electrode and the distal left ventricular electrode 18. The second bioelectric lead field 24 (which may be associated with voltage measurement electrodes, for example) may similarly be defined as the field of current density vectors resulting from a unity current injection between the right atrial electrode 20 and the proximal left ventricular electrode 16. For an overview of bioelectric lead field theory, see sections 11.6.2 and 25.2.1 of J. Malmivuo & R. Plonsey, *Bioelectromagnetism: Principles and Applications of Bioelectric Fields* (1995) (available at http://butler.c-c.tut.fi/~malmivuoIbem/bembook/), beginning at pages 202 and 405, respectively.

The illustrative electrode configuration shown in FIG. 1 may operate as an impedance measurement configuration, for example, with the pulse generator injecting an electrical current between the can electrode and the distal left ventricular electrode 18, the voltage sense circuit measuring a resulting voltage between the right atrial electrode 20 and the proximal left ventricular electrode 16, and the impedance computation module computing an impedance by taking the ratio of the measured voltage to the injected current. Because the convergent bioelectric lead field system shown in FIG. 1 concentrates sensitivity primarily near the region of interest, false alarms triggered by measured impedance changes resulting from resistivity changes in regions of non-interest may be avoided.

Figure 2:
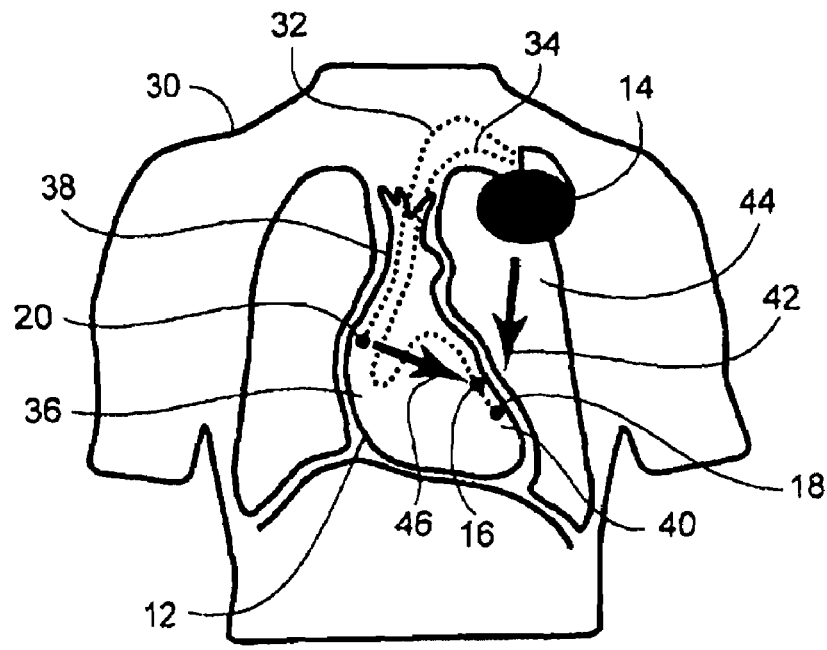
FIGS. 2-4 are perspective diagrams of systems including convergent bioelectric lead field electrode configurations for measuring lung impedance and myocardial impedance.

FIG. 2 illustrates a convergent bioelectric field electrode configuration that is highly sensitive to changes in lung resistivity, and can be used for pulmonary edema detection and assessment. Pulmonary edema may be detected and assessed by making impedance measurements and noting impedance changes. Such impedance changes may indicate an increased presence of fluid within the lungs—that is, pulmonary edema or its onset—and may permit timely therapeutic interventions with early detection. Referring again to FIG. 2, a body 30 with an IMD 14 implanted in a left pectoral region of the body is shown. Leads 32, 34 are connected to ports of the IMD 14, and extend therefrom. The leads 32, 34 each house one or more conductors that electrically connect the IMD 14 to electrodes 20, 16, 18 implanted within a heart 12 of the body 30.

In this illustrative configuration, lead 32 is a right atrial lead, and has, near a distal end, a right atrium electrode 20 positioned in a right atrium 36 of the heart 12. Right atrial lead 32 extends from a port on IMD 14, is introduced to the venous system, down a superior vena cava (SVC) 38, and into the right atrium 36. Right atrium electrode 20 may be either a ring electrode or a tip electrode, or may be located elsewhere along lead 32, such as anywhere in the SVC 38 or innominate veins. Lead 34 is a left ventricular lead, and includes a proximal left ventricular electrode 16 and a distal left ventricular electrode 18, each positioned epicardially over a left ventricle 40 of the heart 12. Left ventricular lead 34 extends from a port on IMD 14, is introduced to the venous system, down the SVC 38, into the right atrium 36, into a coronary sinus and then further into coronary veins which run epicardially over the left ventricle 40. Left ventricular electrodes 16, 18 may be either ring or tip electrodes, or may be located elsewhere along lead 34. While left ventricular lead 34 is shown as a bipolar lead in FIG. 2, the lead 34 may optionally include additional electrodes, and the lead 34 may follow a different path through the heart 12. For example, left ventricular lead 34 may include three, four, five, or more electrodes, and they may be collinearly aligned. Similarly, right atrial lead 32 may include additional electrodes, and may follow a different path through the heart 12 from that shown in FIG. 2. In one embodiment, the left ventricular electrodes 16, 18 are separated by about 15 mm, and the distance between the can electrode and the right atrium electrode 20 is about 10 cm. In other embodiments, the distance between the can electrode and the right atrium electrode 20 may be about 8-15 cm. Similarly, in other embodiments the left ventricular inter-electrode spacing may be about 25 mm, and may range from about 5 mm to about 30 mm.

IMD 14 includes a can electrode on an exterior surface of the device 14. IMD 14 may alternatively or additionally include a button or header electrode, or other type of electrode or electrodes. In the tetrapolar configuration shown in FIG. 2, a pulse generator within the IMD 14 may inject an electrical current between the can electrode located on an external surface of the IMD 14 and the distal left ventricular electrode 18. The injected current flows through at least a portion of a left lung 44, and induces a potential difference (voltage) that may be measured by the right atrial electrode 20 and the proximal left ventricular electrode 16. An impedance computation module within the IMD 14 may then calculate an impedance by computing a ratio of the measured voltage to the injected current. This impedance may be used to assess pulmonary edema within the body 30, as will be described in more detail later. Arrows 42, 46 indicate the general orientation of the two bioelectric lead fields in this configuration. Lead field 42 corresponds to current injection and lead field 46 corresponds to voltage measurement. As seen in FIG. 2, the lead fields 42, 46 converge near the left ventricular wall and left lung, but are substantially separated otherwise.

Figure 3:
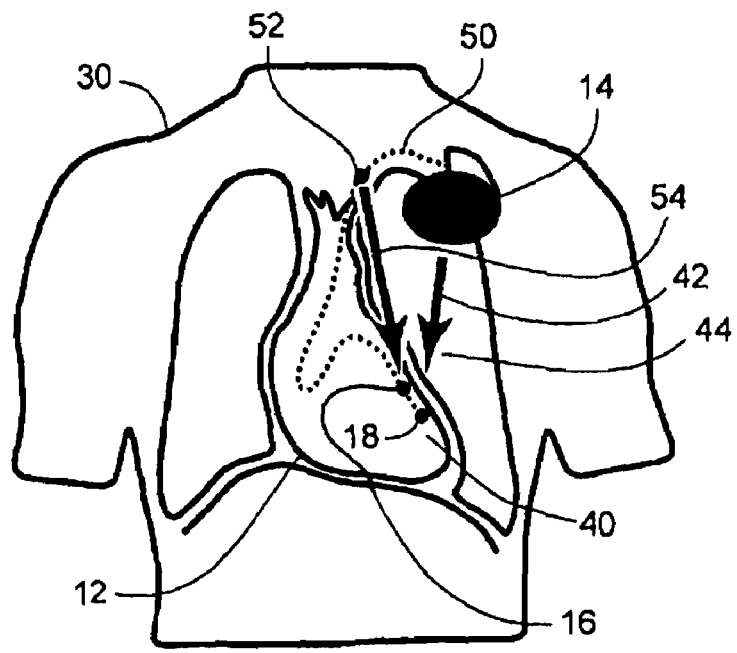

Referring now to FIG. 3, another convergent bioelectric field electrode configuration that is highly sensitive to changes in lung resistivity is illustrated. A left ventricular lead 50 is connected to a port of IMD 14, and includes three electrodes 16, 18, 52. Left ventricular lead 50 is a tripolar lead and follows a similar routing path as the left ventricular lead 34 shown in FIG. 2. In addition to left ventricular proximal and distal electrodes 16, 18, each positioned epicardially over the wall of the left ventricle 40, lead 50 includes an electrode 52 located in the brachiocepahlic vein (also known as the innominate vein). While the configuration illustrated in FIG. 3 uses a tripolar left ventricular lead 50, other arrangements can be used. For example, the brachiocepahlic electrode 52 may be included instead on a right atrial lead, a right ventricle lead, or on a dedicated lead that terminates in or near the brachiocepahlic vein. The brachiocepahlic electrode 52 may alternatively be located in any practical location or position near the brachiocepahlic vein. In operation, a pulse generator within the IMD 14 may inject an electrical current between the can electrode located on an external surface of the IMD 14 and the distal left ventricular electrode 18. The injected current flows through at least a portion of the left lung 44, and induces a voltage that may be measured by the brachiocepahlic electrode 52 and the proximal left ventricular electrode 16. An impedance computation module within the IMD 14 may then calculate an impedance that can be used to assess pulmonary edema by taking the ratio of the measured voltage to the injected current. Arrows 42, 54 indicate the general orientation of the two bioelectric lead fields in this configuration. Lead field 42 corresponds to current injection and lead field 54 corresponds to voltage measurement. The lead fields 42, 54 converge near the anatomical region of interest, but are substantially separated otherwise. In one embodiment, the left ventricular electrodes 16, 18 are separated by about 15 mm, and the distance between the can electrode and the brachiocepahlic electrode 52 is about 4 cm. In other embodiments, the distance between the can electrode and the brachiocepahlic electrode 52 may be about 5-7 cm. Similarly, in other embodiments the left ventricular inter-electrode spacing may be about 25 mm, and may range from about 5 mm to about 30 mm.

Additional electrodes can be used, such as one or more additional left ventricular electrodes or right atrial electrodes, to make the current injection and voltage measurement. For example, the brachiocepahlic electrode 52 may be included on the right atrial lead 32 shown in FIG. 2, and voltages between the right atrial electrode 20 and the proximal left ventricular electrode 16, and between the brachiocepahlic electrode 52 and the proximal left ventricular electrode 16 may consecutively be measured during a current injection, and respective impedances may be calculated as described above. Then, the impedance computation module within IMD 14 may calculate a weighted average impedance measurement, for example, by averaging the impedance measurements using appropriate weighting factors. This measurement may provide a more global assessment of pulmonary edema.

Figure 4:
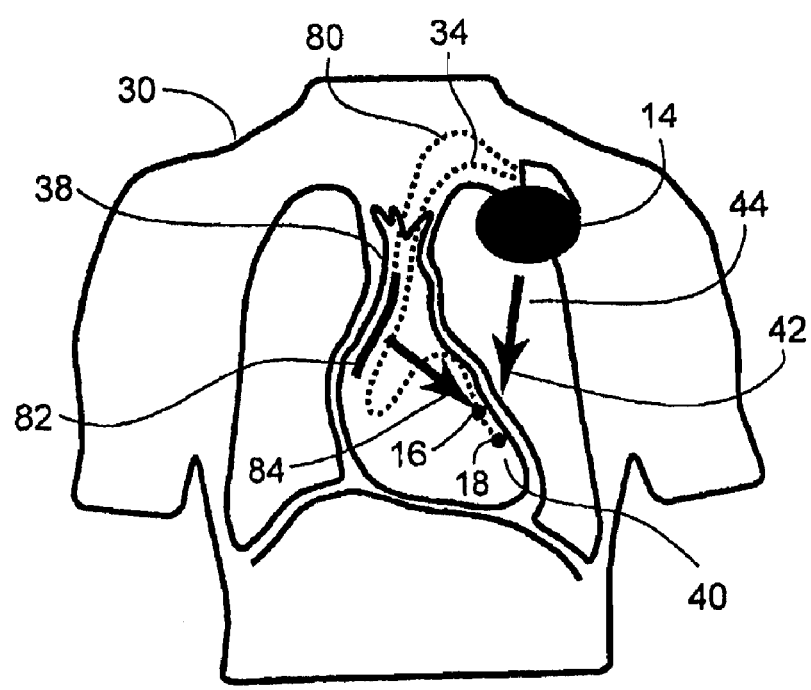

FIG. 4 shows yet another illustrative convergent bioelectric field electrode configuration that is highly sensitive to changes in lung resistivity, and is therefore suited for impedance measurements to assess pulmonary edema. Left ventricular lead 34 extends from a port on IMD 14 and follows the routing path described above with reference to FIG. 2, and has proximal and distal left ventricular electrodes 16, 18, each positioned epicardially over the left ventricle 40. A defibrillator lead 80 is connected to a port of the IMD 14, and includes a defibrillation coil 82 positioned in the superior vena cava 38 of the body 30. The defibrillation coil 82 could alternatively be positioned in the brachiocepahlic vein, subclavian vein, or in another appropriate nearby location. For simplicity, the defibrillator lead 80 is shown terminating at the defibrillation coil electrode 82 in FIG. 4. In practice, the defibrillator lead 80 may extend into the right atrium and right ventricle, and may include a right ventricular defibrillation coil (not shown). Right atrial or right ventricular tip or ring electrodes, or any combination thereof, may also be included.

In operation, a pulse generator within the IMD 14 may inject an electrical current between the can electrode located on an external surface of the IMD 14 and the distal left ventricular electrode 18. The injected current flows through at least a portion of the left lung 44, and induces a voltage that may be measured by the defibrillation coil 82 and the proximal left ventricular electrode 16. An impedance computation module within the IMD 14 may then calculate an impedance that can be used to assess pulmonary edema by taking the ratio of the measured voltage to the injected current. Arrows 42, 84 indicate the general orientation of the two bioelectric lead fields in this configuration. Lead field 42 corresponds to current injection and lead field 84 corresponds to voltage measurement. FIG. 4 shows the convergent disposition of the lead fields 42, 84, which converge near the anatomical region of interest, but are substantially separated otherwise. In one embodiment, the left ventricular electrodes 16, 18 are separated by about 15 mm, and the distance between the can electrode and the defibrillation coil 82 is about 12 cm. In other embodiments, the distance between the can electrode and the defibrillation coil 82 may be about 9-20 cm. Similarly, in other embodiments the left ventricular inter-electrode spacing may be about 25 mm, and may range from about 5 mm to about 30 mm.

In the configuration shown in FIG. 4, IMD 14 may be a defibrillator, and may also perform pacing functions. The leads 34, 80 can include additional electrodes. Combining the measurements from the configurations shown in FIGS. 2-4 is possible. Such impedance measurements may be averaged using appropriate weighting coefficients to obtain a more robust or global impedance value, which may be used to ascertain a more global assessment of pulmonary edema. Moreover, the roles of the current injection electrodes and the voltage measurement electrodes may be exchanged, and equivalent results may be realized. This follows from the reciprocity theorem, which is known to those skilled in the art.

FIG. 5 shows a table 100 of computer simulation results obtained using a computer modeling technique. A three-dimensional computer model obtained with Magnetic Resonance Imaging divides the human thorax into many small volumes, each corresponding to body tissue. The model was used to simulate lung impedance under normal (baseline) and severe pulmonary edema conditions. Each small tissue volume is assigned an appropriate electrical resistivity (e.g. blood=150 ohms-cm, normal lung=1400 ohms-cm, muscle=400 ohms-cm, etc.) according to published tables. Electrodes may then be placed at various locations in the model, and current may be injected. The computer then calculates the resulting voltage potentials at each of the volumes using electric field equations. The results can be used to compute impedance by dividing the measured potentials by the injected current. Using the convergent bioelectric field electrode configurations shown in FIGS. 2-4, the computer simulations used a bipolar left ventricular lead, with current injection between a distal left ventricular coronary vein electrode and a can electrode of an IMD implanted in a left pectoral region. Voltage measurements were then made between a proximal left ventricular coronary vein electrode and a fourth electrode, located in various positions within or near the heart to simulate several configurations. Each of the rows 102 in table 100 represents a different convergent bioelectric field electrode configuration, corresponding to the configurations shown in FIGS. 2-4.

The first row 102*a* displays data for a configuration that locates the fourth electrode in the brachiocepahlic vein, and includes a spacing of 15 mm between the left ventricular electrodes (that is, the proximal and distal left ventricular coronary vein electrodes are separated by 15 mm). The second row 102*b* represents a similar configuration, but with a 25 mm spacing between the left ventricular electrodes. Rows 102*a* and 102*b* present simulation data for the configuration depicted and described above with respect to FIG. 3. The third and fourth rows 102*c*, 102*d* present data for a configuration having the fourth electrode in a superior vena cava to simulate the configuration depicted in FIG. 4. Data in row 102*c* corresponds to a higher fourth electrode coil implant location within the SVC, while data in row 102*d* corresponds to a lower fourth electrode coil implant location within the SVC, a variation that may occur in medical practice to obtain adequate defibrillation thresholds. The fifth and sixth rows 102*e*, 102*f* present data for a configuration with the fourth electrode in a right atrium to simulate the configuration depicted in FIG. 2. Row 102*e* simulates a 15 mm left ventricular electrode spacing arrangement, while row 102*f* simulates a 25 mm spacing arrangement. Measurements were made in simulations at end diastole.

The model simulates pulmonary edema by gradually decreasing the resistivity of model volumes corresponding to lung tissue, for example, from 1400 ohm-cm (healthy) down to 350 ohm-cm (severe edema). As seen in the table 100, for a given configuration, impedance measurements for an edematous patient are less than the corresponding measurement for a normal patient. For example, a normal patient has an impedance measurement of 34.62 ohms at end diastole with the brachiocepahlic, 15 mm configuration (row 102*a*), versus a measurement of 22.61 ohms for an edematous patient, a change of 34.69%. Similarly, impedance changes of 40.67% for the brachiocepahlic, 25 mm configuration (row 102*b*), 40.67% and 45.08% for the SVC configurations (rows, 102*c*, 102*d*, respectively), and 34.44% and 51.60% for the right atrium configurations (rows 102*e*, 102*f*, respectively) were computed.

Figure 6:
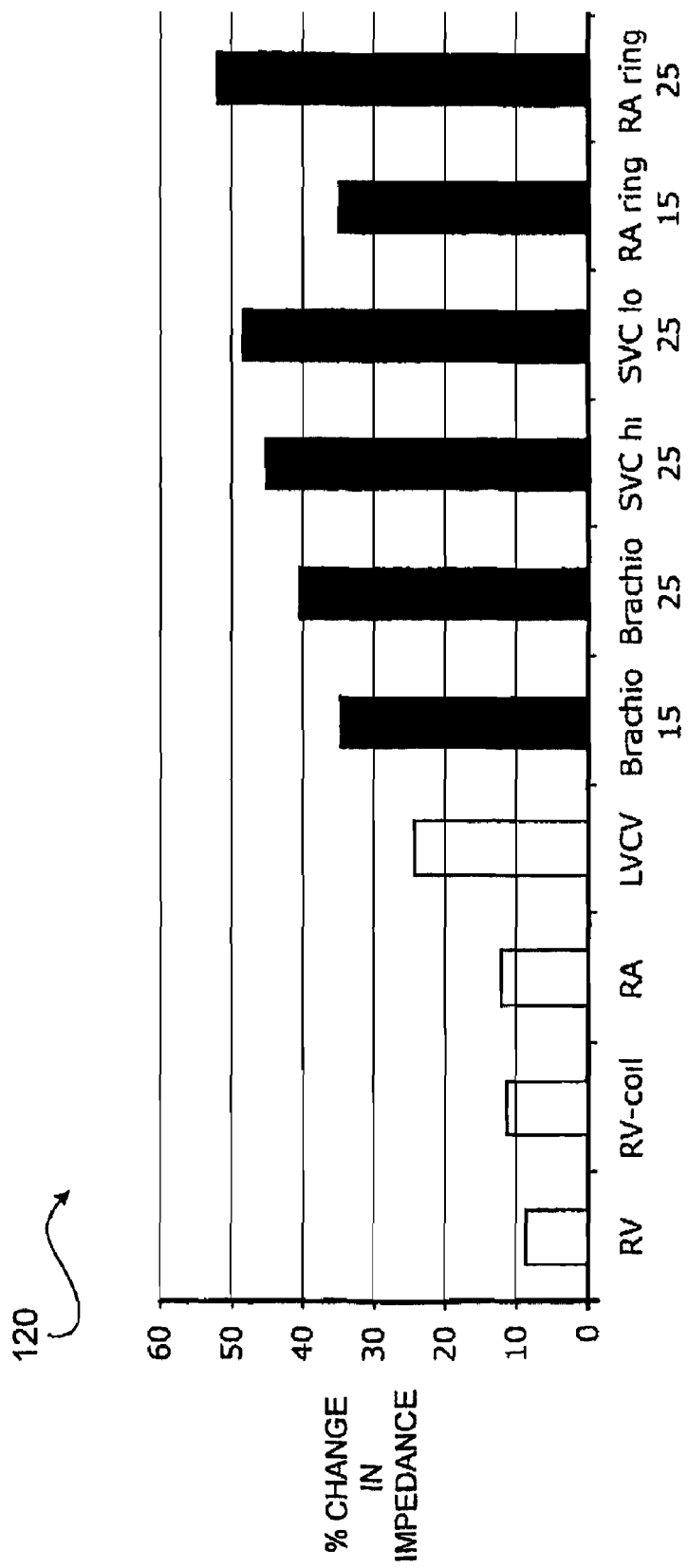
FIG. 6 is a chart of the results from FIG. 5.

FIG. 6 is a bar chart 120 that highlights advantages of the invention by comparing the simulated impedance percentage changes of four tripolar, non-convergent configurations (labeled RV, RV-coil, RA, LVCV) described in U.S. patent application Ser. No. 10/303,305, filed on Nov. 25, 2002, by Andres Belalcazar and Robert Patterson (the present inventors), and Rebecca Shult with the tetrapolar convergent bioelectric field electrode configurations described above in this document. The vertical measure of the bars on the chart 120 indicates the percentage change in measured impedance between a healthy and edematous state in a given patient. The six rightmost columns in the chart 120 correspond to the convergent bioelectric field electrode configurations described above with reference to table 100 of FIG. 5. As seen in FIG. 6, each of the convergent bioelectric field electrode configurations provides a marked increase in sensitivity to lung changes when compared to the non-convergent configurations. For example, the simulated tripolar configurations measured impedance changes of approximately 9% (RV), 11% (RV-coil), 12% (RA), and 24% (LVCV), while the convergent bioelectric field electrode configurations measured impedance changes of 34.69% (Brachio ring, 15 mm), 40.67% (Brachio ring, 25 mm), 45.08% (SVC high, 25 mm), 48.50% (SVC low, 25 mm), 34.44% (RA ring, 15 mm), and 51.60% (RA ring, 25 mm). As such, impedance measurements made using these convergent bioelectric field electrode configurations may provide improved sensitivity to lung resistivity changes, which may permit improved pulmonary edema assessments.

Figure 7:
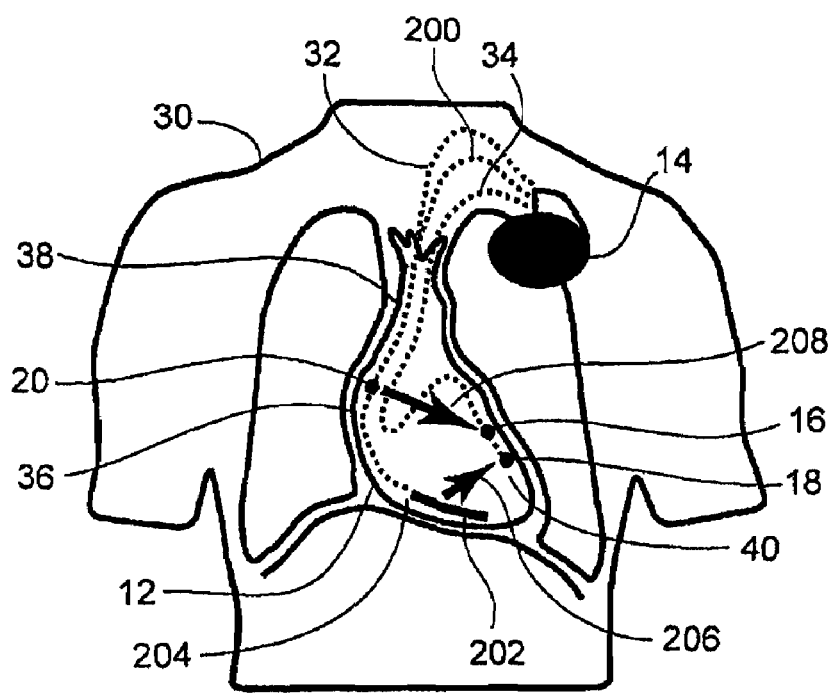
FIGS. 7-9 are perspective diagrams of systems including convergent bioelectric lead field electrode configurations for measuring myocardial impedance.
Figure 8:
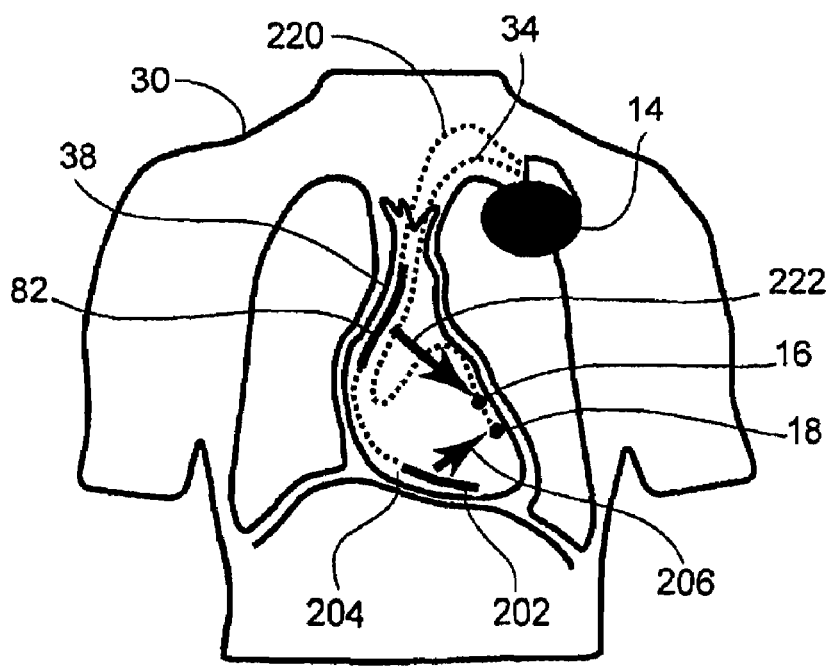
Figure 9:
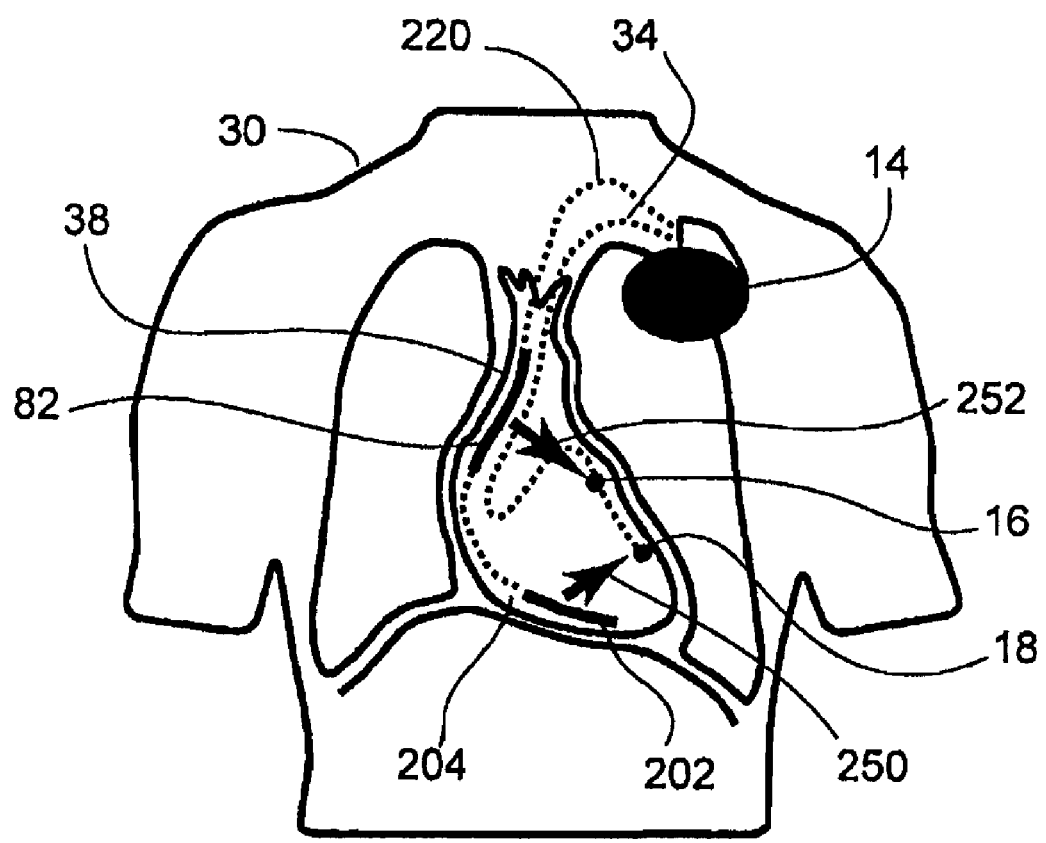

FIGS. 7-9 illustrate convergent bioelectric field electrode configurations that are highly sensitive to changes in myocardium resistivity of the left ventricle, and can be used for myocardial ischemia detection and assessment. Myocardial ischemia or an acute ischemic event (heart attack) may be detected and assessed by measuring myocardial impedance and noting impedance changes. Such impedance changes may be indicative of an ischemic event, as might occur when a plaque within a coronary vessel ruptures and causes a thrombotic occlusion, for example. It is known that the resistivity of the myocardium increases during an ischemic event; for example, the resistivity of the myocardium may approximately double during an acute ischemic event. See Yolocuauhtli Salazar et al., *Transmural Versus Nontransmural In Situ Electrical Impedance Spectrum for Healthy, Ischemic, and Healed Myocardium*, 51 IEEE Transactions on Biomedical Engineering 1421, August 2004. Timely detection of such impedance changes may permit thrombolytic or angioplastic therapeutic interventions that may prevent or minimize permanent myocardial damage caused by the ischemic event, and may prevent a consequent ventricular fibrillation. Early detection may even save lives. Patients treated in this way may represent a cost reduction to the health care system compared to patients who sustain more serious heart damage. Moreover, impedance measurements using the configurations depicted in FIGS. 7-9 may be used to monitor myocardial tissue following an ischemic event to monitor how well the tissue is healing, and whether scarring develops. This follows because scarred tissue has a resistivity of about half the resistivity of healthy myocardium. See Salazar et al., supra. As such, abnormally low impedance measurements following an ischemic event may indicate tissue scarring.

Referring now to FIG. 7, a body 30 with an IMD 14 implanted in a left pectoral region of the body 30 is shown. IMD 14 may be a pacemaker, defibrillator, a combination thereof, or any other type of implantable medical device capable of delivering current stimulation to thoracic tissue and measuring voltage potentials. Leads 32, 200, 34 are connected to ports of the IMD 14, and extend therefrom. The leads 32, 200, 34 each house one or more conductors that electrically connect the IMD 14 to electrodes 20, 16, 18, 202 implanted within the heart 12.

In this illustrative configuration, lead 32 is a right atrium lead, and includes a right atrial electrode 20 positioned in the right atrium 36. Lead 200 is a defibrillation lead, and has, near a distal end, a defibrillation coil 202 positioned in a right ventricle 204 of the heart 12. Defibrillation lead 200 extends from a port on IMD 14, is introduced to the venous system, down the SVC 38, into the right atrium 36, and into the right ventricle 204. Right atrium electrode 20 may be either a ring electrode or a tip electrode. Alternatively, right atrium electrode 20 could be included on another lead, such as a right ventricular lead or a left ventricular lead. Lead 34 is a left ventricular lead, and has a proximal left ventricular electrode 16 and a distal left ventricular electrode 18, each positioned epicardially over the left ventricle 40 of the heart 12. Left ventricular lead 34 extends from a port on IMD 14, is introduced to the venous system, down the SVC 38, into the right atrium 36, into a coronary sinus and then further into coronary veins which run epicardially over left ventricle 40. Left ventricular electrodes 16, 18 may be either ring or tip electrodes, or may be located elsewhere along lead 34. While the left ventricular lead 34 is shown as a bipolar lead in FIG. 7, the lead 34 may optionally include additional or fewer electrodes, and the lead 34 may follow a different path through the heart 12. For example, left ventricular lead 34 may include three, four, five, or more electrodes, and they may be collinearly aligned. In one embodiment, interelectrode spacing between left ventricular electrodes 16, 18 is about 10-15 mm, or approximately one-sixth of the distance from the apex of the heart to the base of the heart. These dimensions may be appropriate for a heart with an apex-to-base length of about 8 cm. Other inter-electrode spacings can be used to maintain the ratio of about one-sixth for hearts of various sizes to facilitate proportional lead field coverage across the left ventricle. Defibrillation lead 200 may also include additional or fewer electrodes, and may follow a different path through the heart 12 from that shown in FIG. 7.

In the configuration shown in FIG. 7, a pulse generator within the IMD 14 may inject an electrical current between the defibrillation coil electrode 202 located in the right ventricle 204 and the distal left ventricular electrode 18. The injected current flows through at least a portion of the myocardium, and induces a potential difference that may be measured by the right atrial electrode 20 and the proximal left ventricular electrode 16.

An impedance computation module within the IMD 14 may then calculate an impedance by computing a ratio of the measured potential difference to the injected current. This impedance may be used to assess myocardial ischemia within the body 30, as will be described in more detail later. Arrows 206, 208 indicate the general orientation of the two bioelectric lead fields in this configuration. Lead field 206 corresponds to current injection and lead field 208 corresponds to voltage measurement, and they converge near the anatomical region of interest—the myocardium of the left ventricular wall—but are substantially separated otherwise. In one embodiment, the left ventricular electrodes 16, 18 are separated by about 15 mm, and the distance between the right atrium electrode 20 and the defibrillation coil 202 is about 10 cm. In other embodiments, the distance between the right atrium electrode 20 and the defibrillation coil 202 may be about 4-12 cm. Similarly, in other embodiments the left ventricular inter-electrode spacing may be about 25 mm, and may range from about 5 mm to about 30 mm.

FIG. 8 shows a configuration that includes a defibrillation lead 220 attached to a port of the IMD 14, and having both a proximal defibrillation coil 82 located in the SVC 38, and a distal defibrillation coil 202 located in the right ventricle 204. A pulse generator within the IMD 14 may inject an electrical current between the distal defibrillation coil electrode 202 located in the right ventricle 204 and the distal left ventricular electrode 18. The injected current flows through at least a portion of the myocardium, and induces a potential difference that may be measured by the proximal defibrillation coil 82 located in the SVC 38 and the proximal left ventricular electrode 16. An impedance computation module within the IMD 14 may then calculate an impedance by computing a ratio of the measured potential difference to the injected current. Arrows 206, 222 indicate the general orientation of the two bioelectric lead fields in this configuration. Lead field 206 corresponds to current injection and lead field 222 corresponds to voltage measurement. The lead fields 206, 222 converge near the anatomical region of interest, but are substantially separated otherwise. In one embodiment, the left ventricular electrodes 16, 18 are separated by about 15 mm, and the distance between the proximal defibrillation coil 82 and the distal defibrillation coil 202 is about 10 cm. In other embodiments, the distance between the proximal defibrillation coil 82 and the distal defibrillation coil 202 is may be about 4-12 cm. Similarly, in other embodiments the left ventricular inter-electrode spacing may be about 25 mm, and may range from about 5 mm to about 30 mm.

The configuration shown in FIG. 9 is similar to the configuration depicted in FIG. 8, but in FIG. 9 the left ventricular coronary vein electrodes 16, 18 are shown separated by a larger distance. In one embodiment, the proximal left ventricular electrode 16 and the distal left ventricular electrode 18 are separated by 25 mm on left ventricular lead 34. This dimension corresponds to a ratio of about one-third, relative to the length of a heart having base-to-apex length of 8 cm. Other embodiments could maintain this same ratio with hearts of other sizes to obtain similar proportional coverage of the lead fields over the left ventricular wall. In other embodiments, the left ventricular electrodes 16, 18 may be separated by 5 mm, 8 mm, 10 mm, 15 mm, 20 mm, 30 mm, or any other appropriate distance, such as any distance between 5 mm and 30 mm. A pulse generator within the IMD 14 may inject an electrical current between the distal defibrillation coil electrode 202 located in the right ventricle 204 and the distal left ventricular electrode 18. The injected current flows through at least a portion of the myocardium, and induces a potential difference that may be measured by the proximal defibrillation coil 82 located in the SVC 38 and the proximal left ventricular electrode 16. An impedance computation module within the IMD 14 may then calculate an impedance by computing a ratio of the measured potential difference to the injected current. Arrows 250, 252 indicate the general orientation of the two bioelectric lead fields in this configuration. Lead field 250 corresponds to current injection and lead field 252 corresponds to voltage measurement. The lead fields 250, 252 converge near the anatomical region of interest, and are substantially separated otherwise, which may enable sensitive and specific pathology detection within the region of interest, and may provide improved transparency to resistivity changes outside of the region of interest.

Like the configurations depicted in FIGS. 7-9, the convergent tetrapolar configurations described above with reference to FIGS. 2-4 can also be advantageously employed to make impedance measurements useful for assessing ischemia. The configurations shown in FIGS. 2-4 are highly sensitive to changes in myocardium resistivity of the left ventricle, and can therefore be used for myocardial ischemia detection and assessment. An impedance computation module within the IMD 14 may calculate an impedance by taking the ratio of the measured voltage to the injected current, and this impedance measurement can be used to detect and assess myocardial ischemia. Moreover, impedance measurements using the configurations depicted in FIGS. 2-4 may be used to monitor myocardial tissue following an ischemic event to monitor how well the tissue is healing, and whether scarring develops.

Figure 10:
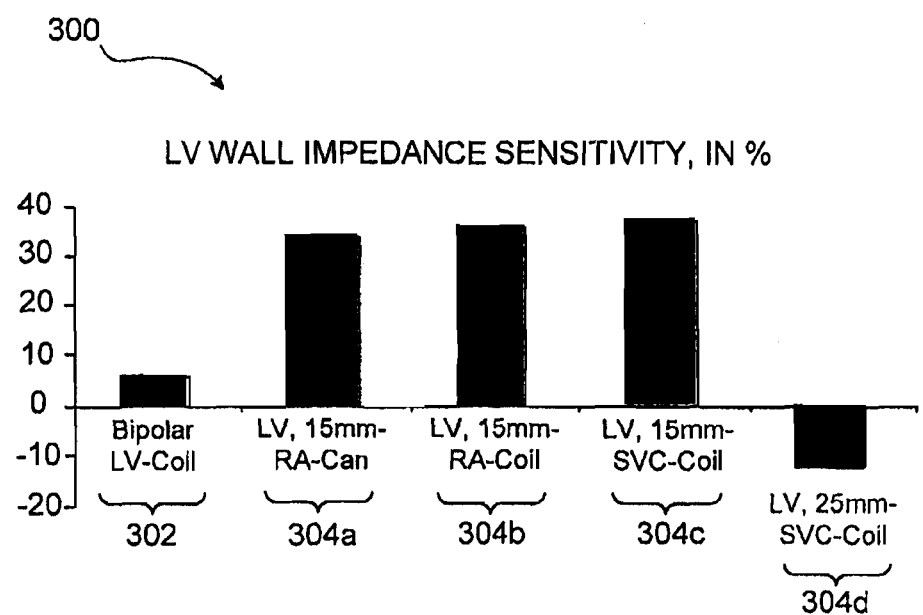
FIG. 10 is a chart of simulation results.

FIG. 10 is a bar chart 300 that highlights advantages of the invention by comparing the simulated left ventricular wall impedance sensitivity percentages of a non-convergent bipolar impedance configuration (bar 302, labeled Bipolar LV-Coil), with tetrapolar convergent bioelectric field electrode configurations (bars 304) described in reference to FIG. 2 and FIGS. 7-9 above. Bar 304*a* corresponds to the configuration described above in reference to FIG. 2, bar 304*b* corresponds to the configuration described above with reference to FIG. 7, bar 304*c* corresponds to the configuration described with reference to FIG. 8, and bar 304*d* corresponds to the configuration described with reference to FIG. 9. The vertical measure of the bars on the chart 300 indicates the left ventricular wall impedance sensitivity. As seen in FIG. 10, each of the convergent bioelectric field electrode configurations (bars 304) provides a marked increase in left ventricular wall impedance sensitivity when compared to the non-convergent configuration (bar 302). For example, the simulated bipolar configuration (bar 302) has approximately a 6% sensitivity to left ventricular wall myocardium, while the convergent bioelectric field electrode configurations have about 34% (bar 304*a*), 35% (bar 304*b*), and 36% (bar 304*c*), and −11% (bar 304*d*) sensitivity. A negative sensitivity indicates that measured impedance will fall when left ventricular wall resistivity rises, and vice versa. As such, impedance measurements made using these convergent bioelectric field electrode configurations may provide improved sensitivity to left ventricular wall resistivity changes, which may permit improved ischemia assessments.

FIG. 11 is a block diagram circuit representation of the implantable device 14 from FIGS. 1-4 and 7-9. FIG. 11 will be described below with reference to the configuration shown in FIG. 2, but it will be understood by those skilled in the art that the description is also applicable to the other configurations shown and described in this document. Device 14 includes circuits for measuring impedance and making pulmonary edema and myocardial ischemia assessments, and communication circuits for interfacing with external devices. An impedance measuring circuit 302 includes a current generator 304, which may inject an electrical current between any two electrodes; for example, the current generator 304 may inject current between the can electrode located on the external surface of IMD 14 and the distal left ventricular coronary vein electrode 18 (FIG. 2). A switch 306 operates in a manner known in the art to direct the current to the appropriate port or ports 308. The current travels from the appropriate port through conductors in the leads to the appropriate electrode. The injection current may be an alternating current (AC) to avoid undesirable polarization and electrolytic degradation effects at the electrodes, and should be of such magnitude, frequency, and duration that it does not cause cardiac stimulation. In one implementation, the AC current may have a frequency of about 50 KHz-100 KHz. Examples of possible current waveforms include sine waves and biphasic pulses (symmetric or otherwise).

The injection current between the can electrode and electrode 18 (see FIG. 2) creates an electric field in the body of a patient. Thus, a voltage potential appears between the right atrial electrode 20 and the proximal left ventricular coronary vein electrode 16. A voltage amplifier 310 may then measure this voltage between electrodes 20 and 16 over conductors in the leads and through ports 308 and the switch 306. The voltage amplifier 310 may, for example, be a signal-conditioning unit to measure the voltage, and may optionally include a demodulator. Alternatively, the roles of the proximal and distal left ventricular coronary vein electrodes 16, 18 could be reversed, with the appropriate wiring modifications.

A control block 312 receives or contains information on the magnitudes of both the injected current and the resulting measured voltage. Analog-to-digital (A/D) converters (not shown), within or outside of the control block 312, may be used to translate the information. A processing unit (not shown) such as a microprocessor, microcontroller, or digital signal processor within the control block 312 may then use the current and voltage information to calculate impedance by dividing voltage by current. As body tissue fluid levels increase, the tissue impedance decreases. Thus, the impedance ratio may be used to assess pulmonary edema, and a degree of pulmonary edema may be determined for the patient. An algorithm describing the edema value determination will be discussed later. Conversely, myocardial tissue impedance increases during an ischemic event. Thus, the impedance value may be used to assess myocardial ischemia, and an in-progress ischemic event may be detected for the patient. An algorithm describing the ischemia detection will be discussed later.

The control block 312, as is conventional, may additionally include read-only memory (ROM), random-access memory (RAM), flash memory, EEPROM memory, and the like, which may store instructions that may be executed by the processing unit, as well as digital-to analog (D/A) converters, timers, counters, filters, switches, etc. (not shown). Impedance measurements, edema values, and ischemia values may also be stored in memory. These control block components may be integrated within a single device, such as an application specific integrated circuit (ASIC), or alternatively may be separate devices. Appropriate busses (not shown) allow communication between components within control block 312.

Information from a sensor block 314 may be used to adjust the relationship between the measured impedance and the degree of edema or ischemia. A posture sensor 316 may provide patient orientation information to the control block 312, allowing posture compensation to be included in the assessment of edema or ischemia. Because organs and excess fluid in the thorax and lungs shifts with posture changes due to gravity, measured impedance may vary as a patient assumes different positions. For example, when a patient lies on his/her right side, fluid and tissues in the left lung 44 may gravitate towards the mediastinum near the left ventricular coronary vein electrodes 16, 18 resulting in lower measured impedance. Thus, based on posture sensor information, the relationship between the impedance measurement and the degree of edema or ischemia may be adjusted to compensate. Similarly, that relationship may be inversely adjusted for a patient lying on his/her left side. Several types of posture sensors could be used, including mercury switches, DC-accelerometers, or other piezoelectric devices.

An activity sensor 318, conventionally used to aid in pacing applications, may also provide information to the control block 312. By using these compensation schemes, edema and ischemia interpretation errors caused by postural fluid shifts within a patient may be avoided. Either sensor 316, 318 may optionally be excluded from the implantable device 14.

A telemetry block 320 may communicate wirelessly using radio frequency (RF) transmissions over an antenna 322 with a similarly wirelessly equipped external monitoring unit 324. Monitoring unit 324 may be a computer (custom programmer, desktop, laptop, handheld, etc.), a telemedicine home station, a wearable device such as a wristwatch, a mobile phone, a wearable repeater, or any other appropriate device, and may be used to program the implantable device 14, or to retrieve information from the IMD 14, such as impedance measurements, edema values, or ischemia values. This communication link may be used to alert a physician or healthcare provider to an acute ischemic event or to detection of pulmonary edema, for example, such that therapeutic intervention could be promptly initiated. Alternatively, the monitoring unit 324 could utilize a phone connection to dial 9-1-1 and summon an emergency response team, could occasion a similar response by communicating over a network such as the Internet, or could audibly or textually inform the patient to seek medical attention. In this manner, it is possible to continuously monitor the patient for detection of various pathologies, twenty-four hours a day, seven days a week, and to alert a physician or care provider promptly in the event of pathology detection.

A sensing/pacing/defibrillation circuit 330 includes a pacing circuit 332, a defibrillation circuit 334, and a sense amplifier 336, and is used to sense and/or stimulate (pace) cardiac events and manage cardiac rhythms. The generic impedance computation module is not explicitly shown in FIG. 11, but would include several of the FIG. 11 blocks, or portions thereof. A battery 340 supplies power to the various circuits and blocks of IMD 14 (for simplicity, connections are not shown in FIG. 11). Alternatively, the impedance measuring circuit 302 could use the normal cardiac stimulation pulse from the sensing/pacing/defibrillation circuit 330 in lieu of a current injection from pulse generator 304, and measure the resulting voltage. The impedance could then be computed. A further alternative excludes the impedance measuring circuit 302, and uses the Sensing/Pacing/Defibrillation circuit 330 for the current injection and voltage measurement functions necessary for impedance determination.

As previously mentioned, impedance measurements can be affected by resistivity contributions from different organs and/or body tissues. For a given electrode measurement configuration, certain organs or body tissues will contribute more significantly to the total impedance measurement, while other organs/tissues will contribute less significantly. It is desirable for the target organ/tissue to have a large contribution to the impedance measurement, and for all other organs/tissues to have a minimal contribution to the measurement. For example, when measuring impedance to assess pulmonary edema, one would prefer large sensitivity to the lung, and minimal sensitivity to all other thoracic organs/tissues. Similarly, when measuring impedance to assess myocardial ischemia, one would prefer large sensitivity to the myocardium and minimal sensitivity to all other thoracic organs/tissues.

FIG. 12 shows a table 400 of impedance sensitivity coefficient simulation results compiled using the model described above for various electrode configurations. Each configuration is represented by a column 401, 402 in the table 400. Column 401*a* represents a tripolar configuration described in U.S. patent application Ser. No. 10/303,305, filed on Nov. 25, 2002, by Andres Belalcazar and Robert Patterson (the present inventors), and Rebecca Shult, column 401*b* represents a known configuration, and columns 402*a*-402*e* represent convergent bioelectric lead field electrode configurations described in this document. Columns 402*a* and 402*b* correspond to the configuration described above with reference to FIG. 3; column 402*c* corresponds to the configuration described above with reference to FIG. 4; and columns 402*d* and 402*e* correspond to the configuration described above with reference to FIG. 2. For each configuration 401, 402, table 400 shows a quantification of the contributions of several thoracic organs and tissues to the total impedance measured by the configuration. The higher the magnitude of the coefficient, the more significantly it contributes to the total impedance. When monitoring the lung, for example, it is desirable for the lung coefficient be as high as possible, and for all of the other coefficients to be relatively low. This assures that measured impedance changes are lung-specific, and largely the result of lung impedance changes, as desired. Similarly, for monitoring the left ventricular wall, a high left ventricular wall coefficient is desired, with the other coefficients being low.

Table 400 shows that, using the convergent bioelectric field electrode configurations (columns 402*a*-402*e*), sensitivity to fat (row 403) and muscle (row 404) near the IMD 14 is diminished by nearly ten times (e.g., from 0.2199 and 0.1888 in the tripolar configurations (columns 401*a*, 401*b*) to less than 0.022 in the convergent tetrapolar configurations (columns 402*a*-402*e*)). As such, the convergent bioelectric field electrode configurations are more immune to postural or other changes of the shoulder and pectoral region. This lost sensitivity results in greater sensitivity to other areas, in particular, to the left ventricular wall and blood (row 406), as well as to the left lung (row 405), as desired. Thus, these configurations will be less susceptible to impedance changes caused by arm or shoulder movements which expand or contract the pectoral muscle near the IMD 14, or to edema in the pectoral muscles, and will be more sensitive to impedance changes cause by the left lung and the left ventricular wall, and will therefore be better able to detect and assess pulmonary edema and ischemia.

Table 400 also shows that the inter-electrode spacing (15 mm vs. 25 mm) of the left ventricular electrodes 16, 18 is a significant factor. Farther spaced electrodes provide a deeper penetration of the sensing region, which may be desired in the case of lung monitoring, but may not be desired in the case of left ventricular wall monitoring. For example, the brachiocepahlic configuration with a 25 mm left ventricular inter-electrode spacing (column 402*b*) has a left lung (row 405) sensitivity coefficient of 0.3196, versus a coefficient of 0.2548 for a 15 mm spacing (column 402*a*), making it more sensitive to left lung resistivity changes. Similarly, the right atrium 25 mm configuration (column 402*e*) has a left lung (row 405) sensitivity coefficient of 0.4175, versus a coefficient of 0.2493 for a 15 mm spacing (column 402*d*). However, the brachiocepahlic 15 mm configuration (column 402*a*) has a left ventricular lateral wall (row 406) sensitivity coefficient of 0.2514 versus a coefficient of −0.0806 for the 25 mm spacing (column 402b), and the right atrium 15 mm configuration (column 402d) has a 0.3394 coefficient versus a coefficient of −0.1950 for the 25 mm spacing (column 402e), demonstrating better sensitivity to left ventricular wall resistivity changes. As mentioned earlier, the dimensions of 15 mm and 25 mm may be appropriate for a typical heart with apex-to-base dimensions of 8 cm. The inter-electrode spacing can be proportionately altered for hearts of other sizes to assure consistent coverage of the lead fields over tissues of interest, thereby permitting assessment and detection across anatomies of various sizes.

The table 400 was calculated using the computer models of the thorax described above to simulate the lead fields of the configurations. The contribution of each differential volume constituting an organ or tissue was calculated using the volume integral of the Schmitt-Geselowitz equation, shown below in equation 1:

$$Z = \int \rho J_{LE} \cdot J_{LI} dv \quad (1)$$

In equation 1, Z is the impedance (ohms) measured by the measuring device by taking the ratio of measured voltage at the pickup electrodes to the current injected at the excitation electrodes. $\rho$ is the local tissue resistivity at each location (ohms-cm); $J_{LE}$ is the lead field vector (1/cm^2) of the voltage measurement electrode pair; $J_{LI}$ the lead field vector (1/cm^2) of the current injection electrode pair; and dv is the volume integral differential (cm^3). Equation 1 states that integrating the dot product of the lead fields weighted by the tissue resistivity at each location over the volume of each organ gives a value in ohms, which corresponds to the contribution of that organ to the total measured impedance. Dividing an organ's contribution in ohms by the total impedance seen by the system gives the sensitivity coefficient tabulated in table 400. For further details on the meaning of the terms in the above equation, see J. Malmivuo & R. Plonsey, *Bioelectromagnetism: Principles and Applications of Bioelectric Fields* (1995).

Figure 13:
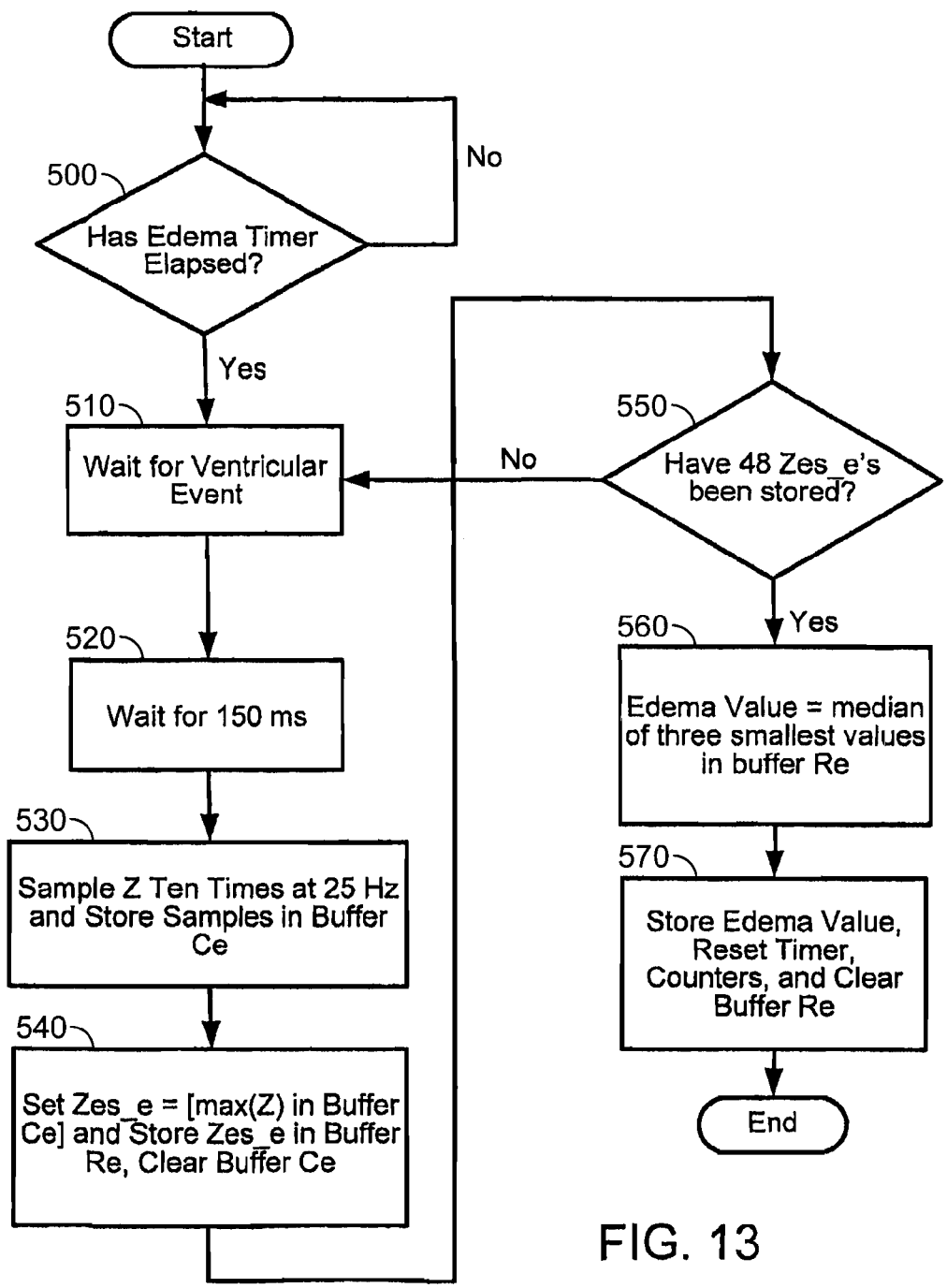
FIG. 13 is a flowchart illustrating how the device of FIG. 11 may make edema assessments.

The flowchart of FIG. 13 is an example of how an algorithm may be implemented in the control block 312 of FIG. 11 to make edema assessments. The process performed by a control block processing unit executing instructions begins, at step 500, with an edema timer (located within control block 312 in the processing unit, for example) implementing a waiting period. This period may be from about 2 hours to about 3 days, as determined by a physician. The value may be programmable over a radio frequency link to telemetry block 320 (FIG. 11).

After the waiting period has elapsed, the control block 312 waits for the next ventricular event in step 510. The ventricular event may be determined using pace timing control information resident in the control block 312, or from the sense amplifier 336 in the sensing/pacing/defibrillation circuit 330 (FIG. 11). The occurrence of a ventricular event indicates that the heart has started its contraction, and prompts a waiting period of about 150 ms in step 520 to allow cardiac contraction to set in. Next, in step 530, impedance is sampled ten times at a rate of 25 Hz, and the impedance samples are stored in a memory buffer Ce (for cardiac/edema). This allows impedance to be sampled before and after a peak of an impedance waveform (that is, a waveform defined by the impedance measurements as constituent points of the waveform), so as to encounter and determine its peak end-systolic value, here referred to as Zes_e (for Z end-systole for edema detect). Zes_e is set equal to the largest of the ten impedance samples in buffer Ce and stored in a memory buffer Re (for respiration/edema), and buffer Ce is cleared at step 540.

At step 550, a counter determines whether forty-eight Zes_e's have yet been stored. If not, steps 510-540 are repeated. In this manner, steps 510-540 are repeated forty-seven times, thereby allowing forty-eight end-systole impedance measurements Zes_e to be stored in buffer Re, sufficient for covering at least about three breath cycles.

Next, at step 560, a pulmonary edema value is assigned the median of the three smallest impedance values (that is, the values corresponding to end-expiration) in buffer Re. The pulmonary edema value may be stored in memory, buffer Re may be cleared, and the appropriate timers and counters reset (570), and the process ends. The process may then begin again at step 500, waiting until the next edema sampling moment. In the interest of stable measurement results and repeatability, measurements may be taken at the same moment in the cardiac and respiratory cycles; for example, measurements may be taken at end-systole and end-expiration (as described above with reference to the flowchart of FIG. 13), or at end-diastole and end-expiration, or at any other point of the cardiac cycle.

The edema value may be compared with a stored edema threshold value, perhaps programmable over the telemetry link, and if the edema value exceeds the threshold value a warning flag may be set, or an alarm triggered. Stored edema values or impedance values may then be transmitted by telemetry block 320 to monitoring station 324 (FIG. 11), for example, when the monitoring station 324 interrogates the device 14. A physician might subsequently analyze the data for trends in edema values.

Figure 14:
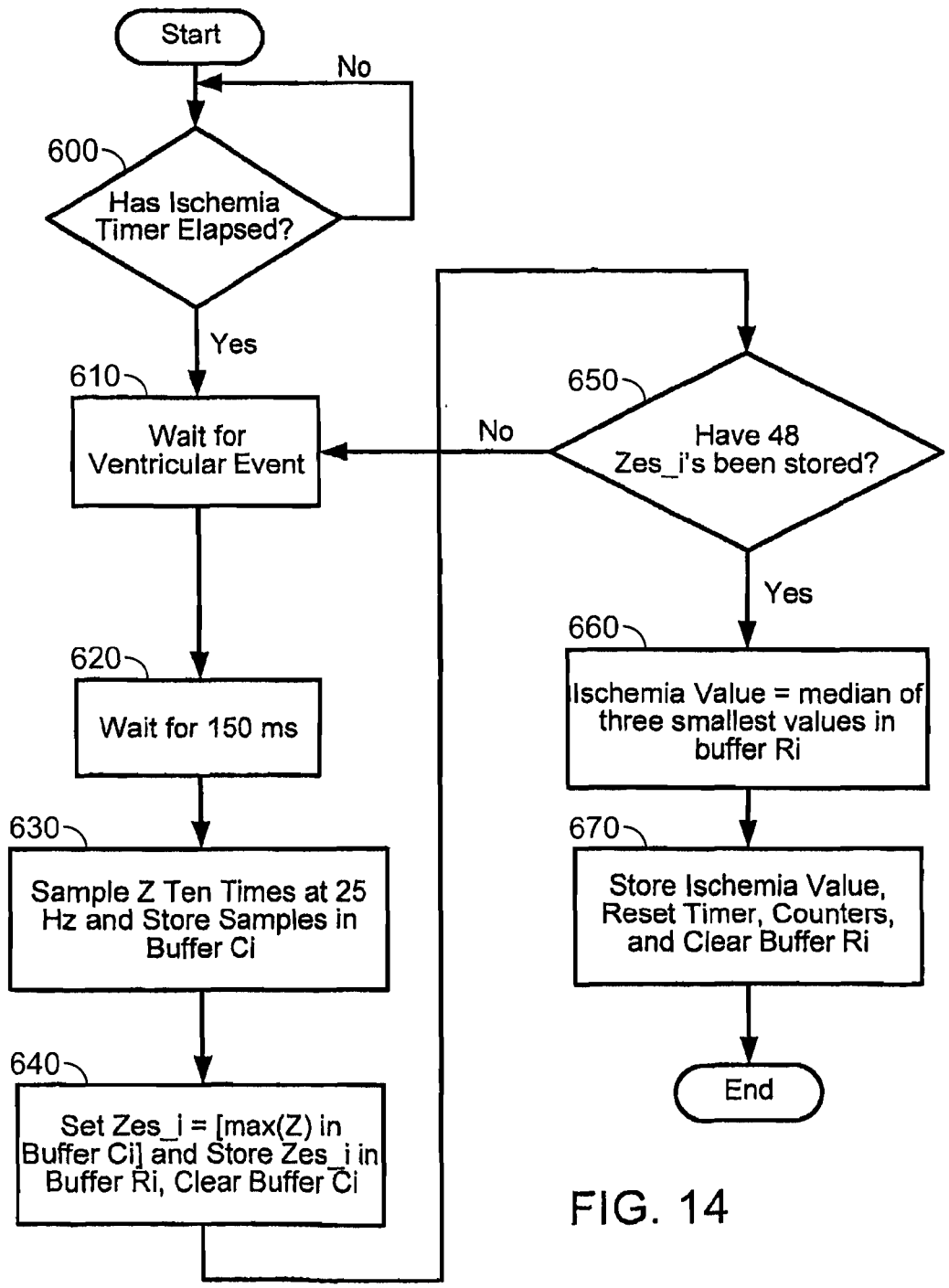
FIG. 14 is a flowchart illustrating how the device of FIG. 11 may make ischemia assessments.

The flowchart of FIG. 14 shows an example of how an algorithm may be implemented in the control block 312 of FIG. 11 to make ischemia assessments. The process performed by a control block processing unit executing instructions begins, at step 600, with an ischemia timer (located within control block 312 in the processing unit, for example) implementing a waiting period. This period may be from about fifteen seconds to about five minutes, as determined by a physician. In an embodiment, the waiting period may be about one minute. The value may be programmable over a radio frequency link to telemetry block 320 (FIG. 11).

Referring again to FIG. 14, after the waiting period has elapsed, the control block 312 waits for the next ventricular event in step 610. The ventricular event may be determined using pace timing control information resident in the control block 312, or from the sense amplifier 336 in the sensing/pacing/defibrillation circuit 330 (FIG. 1).

The occurrence of a ventricular event indicates that the heart has started its contraction, and prompts a waiting period of about 150 ms in step 620 to allow cardiac contraction to set in. Next, in step 630, impedance is sampled ten times at a rate of 25 Hz, and the impedance samples are stored in a memory buffer Ci (for cardiac/ischemia). This allows impedance to be sampled before and after a peak of an impedance waveform (that is, a waveform comprising the impedance measurements as constituent points of the waveform), so as to encounter and determine its peak end-systolic value, here referred to as Zes_i (for Z end-systole for ischemia detect). Zes_i is set equal to the largest of the ten impedance samples in buffer Ci and stored in a memory buffer Ri (for respiration/ischemia), and buffer Ci is cleared at step 640.

At step 650, a counter determines whether forty-eight Zes_i's have yet been stored. If not, steps 610-640 are repeated. In this manner, steps 610-640 are repeated forty-seven times, thereby allowing forty-eight end-systole impedance measurements Zes_i to be stored in buffer Ri, sufficient for covering at least about three breath cycles. Next, at step 660, an ischemia value is assigned the median of the three smallest impedance values (that is, the values corresponding to end-expiration) in buffer Ri. The ischemia value may be stored in memory, buffer Ri may be cleared, and the appropriate timers and counters reset (670), and the process ends. The process may then begin again at step 600, waiting until the next ischemia sampling moment. In the interest of stable measurement results and repeatability, measurements may be taken at the same moment in the cardiac and respiratory cycles; for example, measurements may be taken at end-systole and end-expiration (as described above with reference to the flowchart of FIG. 14), or at end-diastole and end-expiration, or at any other point of the cardiac cycle.

The ischemia value may be compared with a stored ischemia threshold value, perhaps programmable over the telemetry link, and if the ischemia value exceeds the threshold value a warning flag may be set, or an alarm triggered. Stored ischemia values or impedance values may then be transmitted by telemetry block 320 to monitoring station 324 (FIG. 11), for example, when the monitoring station 324 interrogates the device 14. A physician might subsequently analyze the data for trends in ischemia values.

In one implementation, edema or ischemia may be assessed at about the same heart rates and postures. One way this could be accomplished is by executing the steps of the flowcharts shown in FIG. 13 or FIG. 14 only when the heart rate and posture fall within pre-programmed ranges (that is, the steps of one or both of the flowcharts would be executed only when the heart rate and posture are about the same as when the last edema or ischemia assessment was done). Alternatively, the edema and/or ischemia assessments could be stored in memory, along with the corresponding heart rate and posture information, using the processes of FIG. 13 or FIG. 14. The edema and/or ischemia measurements could then later be classified in bins by heart rate range or posture categories, and transmitted or presented to the physician per the category that he/she selects.

Many alternatives are possible for the algorithm. For example, a different number of samples may be taken, sample rates may change, mean averaging may be used in place of median, alternate waiting periods may be chosen, and alternative comparison schemes may be implemented. For example, a single register may be used in place of buffers and, concurrent with sampling, the newly sampled measurement may be compared with an ongoing maximum/minimum value stored in the register. As an alternative to waiting periods, a patient may initiate a series of measurements, for example, with a magnet. Impedance values and sensor information may be used to assign an edema value or an ischemia value that differs from the measured impedance. Of course, time stamps could also be stored with the edema or ischemia values, as well as other relevant information, such as posture information, heart rate, or activity levels, for example. Telemedicine home stations could also initiate a measurement, and then send results to a care center. Impedance measurements may be time-multiplexed with normal cardiac stimulation events. Alternatively, the normal cardiac stimulation pulses may be used in lieu of dedicated impedance-measurement current injections.

Figure 15:
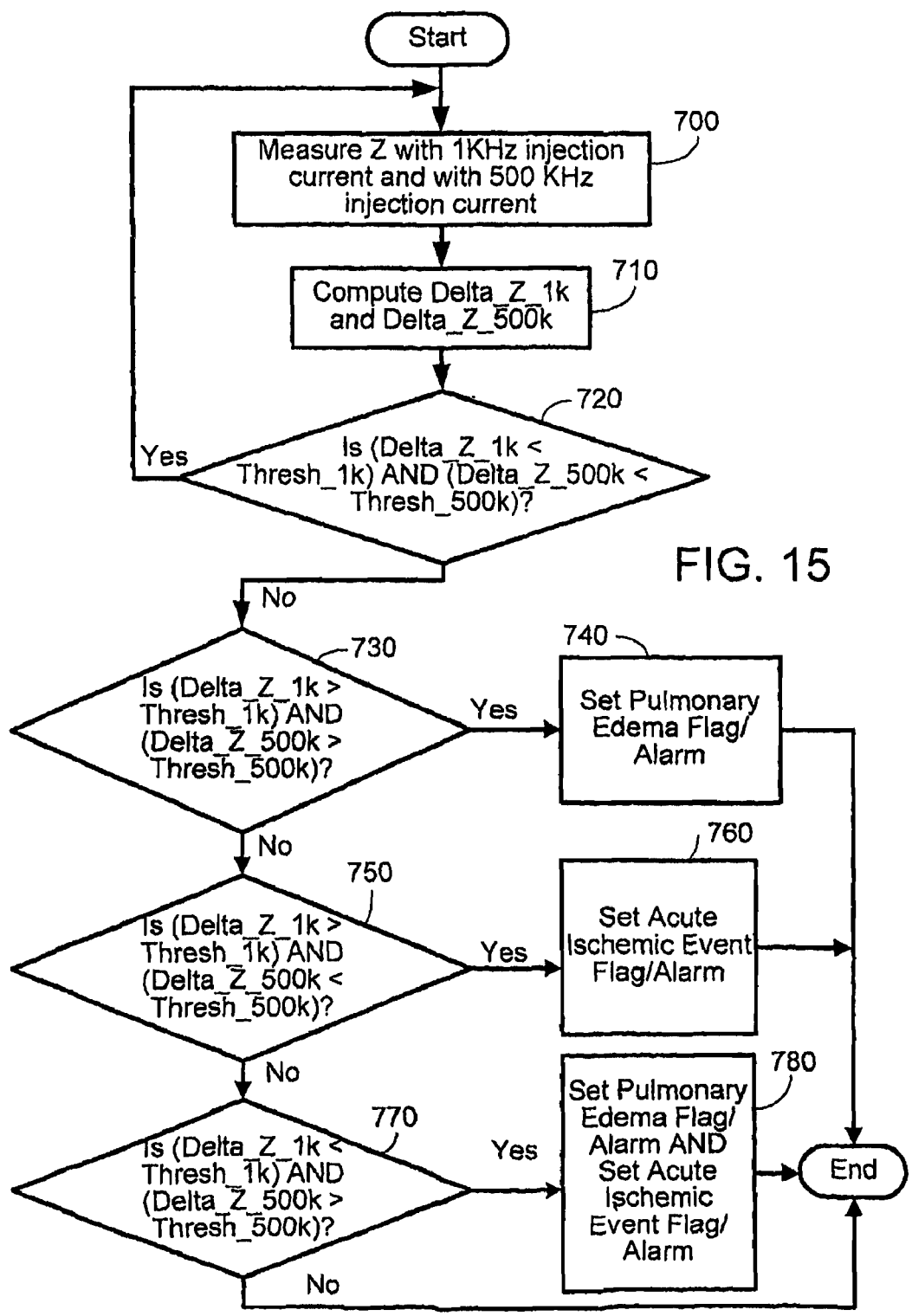
FIG. 15 is a flowchart illustrating how the device of FIG. 11 may make multi-frequency impedance measurements for pathology detection, classification and discrimination.

The flowchart of FIG. 15 shows an example of how an algorithm may be implemented in the control block 312 of FIG. 11 to make impedance measurements at various frequencies to discriminate the effects of various pathologies, such as edema and ischemia, which may have confounding effects at a single frequency measurement. It is known that a myocardium in an ischemic state exhibits substantially different impedance responses at different frequencies, such as between 1 KHz and 500 KHz, while lung tissue and edema fluid do not exhibit much change at frequencies below 1 MHz. See Salazar et al., supra. The degree of myocardial ischemia has little effect on impedance measurements made at 500 KHz, whereas at 1 KHz the degree of ischemia has a significant effect on the impedance. Id. As such, multi-frequency measurements can be taken, and the results can be used to classify impedance changes as resulting from pulmonary edema or myocardial ischemia, for example.

Referring again to FIG. 15, the process performed by a control block processing unit executing instructions begins, at step 700, by making a first impedance measurement with an injection current frequency of 1 KHz, and making a second impedance measurement with an injection current frequency of 500 KHz. The injection currents may be sine waves at 1 KHz and 500 KHz, respectively, or may be any waveforms causing a response similar in frequency content to said sine wave excitations, such as rectangular exponential decay pulses in a monophasic or biphasic form, for example. Next, at step 710, Delta_Z_1 k is computed by taking the absolute value of the difference between the first impedance measurement and a first reference value, and Delta_Z_500 k is computed by taking the absolute value of the difference between the second impedance measurement and a second reference value. The reference values may be programmed by a physician at the time of device 14 implant, or may be updated later by a physician at a follow-up visit, for example. Alternatively, the reference values may be updated by control unit 312 (FIG. 11). For example, the reference values may be updated in response to a calculation performed by control unit 312, such as following a calculation to determine a running average of impedance measurements, or some other adaptive technique.

If Delta_Z_1 k is less than a first threshold value (Thresh_1 k) and, at the same time, Delta_Z_500k is less than a second threshold value (Thresh_500 k) (720), then no urgent condition exists, and the process restarts, perhaps after an appropriate waiting period. Otherwise, at least one of the Delta values has exceeded its corresponding threshold, and edema or ischemia may exist. The process continues at step 730 to determine if either or both of the pathologies are present. If Delta_Z_1 k is greater than Thresh_1 k and Delta_Z_500 k is greater than Thresh_500 k, then a pulmonary edema flag or alarm is set at step 740, and the process ends. However, if the condition at step 730 fails, then only one of the two Deltas has a significant change. If only the low frequency measurement changes significantly, then the change may be due solely to ischemic events, since the high frequency measurement is insensitive to ischemia, as noted earlier. This is implemented in step 750: if Delta_Z_1 k is greater than Thresh_1 k and Delta_Z_500 k is less than Thresh_500 k, then an acute ischemic event flag or alarm is set at step 760, and the process ends. If, on the other hand, only the high frequency measurement changes (e.g., an impedance drop at 500 KHz), the change may be due to edematous events (since ischemia has little effect on impedance measurements at 500 KHz), and an explanation for a concurrent low frequency measurement that has not changed significantly over time may be a simultaneous ischemic event. Under this scenario, ischemia causes an increase in impedance at a low frequency such as 1 KHz, while edema causes a decrease. If both events occur simultaneously, the result may be a cancellation of effects, such that there would be no significant change in the low frequency monitoring. This decision-making step occurs at step 770: if Delta_Z_1 k is less than Thresh_1 k and Delta_Z_500 k is greater than Thresh_500 k, then a pulmonary edema flag or alarm and an acute ischemic event flag or alarm is set at step 780, and the process ends. The flowchart of FIG. 15 describes a process for detection of the onset of edema or ischemic events. Edema clearance or ischemia resolution, or their combination, may be detected with similar processes using similar principles. Thus, the invention permits monitoring, detection, discrimination and classification of both pulmonary edema and myocardial ischemia.

Many variations of the algorithm are possible. For instance, more than two impedance measurements of varying frequency can be made, and alternative frequencies, such as 50 Hz, 500 Hz, 5 KHz, 10 KHz, 50 KHz, 100 KHz, 400 KHz, 600 KHz, 1 MHz, etc., can be used. Rather than injecting two currents at different frequencies, a composite signal current that contains both frequencies could be injected, and additional filtering circuitry in the voltage measurement circuits of device 14 could be used to separate the frequency components. Impedance values obtained using the algorithms described by the flowcharts shown in FIGS. 13-14 could be used. The telemetry module 320 (FIG. 11) could communicate the flags or alarms to a monitoring station 324 (FIG. 11) or to a physician or care provider. The algorithm may be executed at a variety of appropriate time intervals, such as every 15 seconds, every 30 seconds, every minute, every two minutes, every five minutes, every seven minutes, every ten minutes, every hour, or the like. Measurements and computation results may be stored in memory or downloaded to a monitoring station for reference by a physician.

A number of embodiments of the invention have been described. Nevertheless, it will be understood that various modifications may be made without departing from the spirit and scope of the invention. For example, using the principles described above for ischemia detection, the left ventricular wall can also be monitored to detect hypertrophy (wall thickening), which often occurs with hypertension (high blood pressure) or with aortic valve stenosis. Hypertrophy can be an indication that the heart is overloaded, an undesirable condition. The difference in time of onset can be used to distinguish ischemic events from hypertrophic events. Ischemic events are rather quick in onset, whereas hypertrophy generally occurs/resolves over the course of days. Furthermore, the multi-frequency technique described above could be used to rule out ischemia. Polarities of the current injection and voltage measurement may be reversed. Moreover, the roles of the current injection electrodes and the voltage measurement electrodes may be exchanged.

As is well known to those skilled in the art, impedance is a complex quantity defined in the frequency domain, and consists of a magnitude and a phase angle. The impedance magnitude is the ratio of the magnitudes of the measured voltage to the injected current. The impedance phase angle indicates the degree of phase shift between the injected current and the measured voltage. One way of measuring an impedance phase shift is to calculate the amount of time between a peak of the injected current signal and a resulting peak of the measured voltage signal. Any of the configurations shown in FIG. 2-4 or 7-9 may measure either impedance magnitude or impedance phase angle, or both, for pathology assessment and detection. Accordingly, other embodiments are within the scope of the following claims.

What is claimed is:

1. A method of measuring impedance for pathology assessment in a living being, the method comprising:

injecting a current between first and second electrodes implanted in a body of a living being, the first and second electrodes defining a first electric lead field in the body, the first electric lead field oriented between the first and second electrodes;

measuring a potential difference between third and fourth electrodes implanted in the body, the potential difference resulting from the current injected between the first and second electrodes, the third and fourth electrodes defining a second electric lead field in the body, the second electric lead field oriented between the third and fourth electrodes, wherein the first and second electric lead fields converge near an assessment site within the body, but are substantially separated otherwise; and calculating an impedance value based on the potential difference and the current injection, and using the impedance value to assess a pathology near the assessment site.

2. The method of claim 1, wherein the assessment site is not within a heart chamber.

3. The method of claim 2, wherein the assessment site is a left lung and the pathology is pulmonary edema.

4. The method of claim 2, wherein the assessment site is a left ventricular wall of a heart and the pathology is myocardial ischemia.

5. The method of claim 2, wherein the assessment site is a left ventricular wall of a heart and the pathology is left ventricular hypertrophy.

6. The method of claim 1, wherein the second and fourth electrodes are positioned near a left ventricle of a heart, the first electrode is positioned in a pectoral region, and the third electrode is positioned in a right atrium of the heart.

7. The method of claim 1, wherein the second and fourth electrodes are positioned near a left ventricle of a heart, the first electrode is positioned in a pectoral region, and the third electrode is positioned near a brachiocepahlic vein.

8. The method of claim 1, wherein the second and fourth electrodes are positioned near a left ventricle of a heart, the first electrode is positioned in a pectoral region, and the third electrode is positioned in a superior vena cava.

9. The method of claim 1, wherein the second and fourth electrodes are positioned near a left ventricle of a heart, the first electrode is positioned in a right ventricle of the heart, and the third electrode is positioned in a right atrium of the heart.

10. The method of claim 1, wherein the second and fourth electrodes are positioned near a left ventricle of a heart, the first electrode is positioned in a right ventricle of the heart, and the third electrode is positioned in a superior vena cava.

11. The method of claim 1, wherein the second and fourth electrodes are separated by about fifteen millimeters.

12. The method of claim 1, wherein the second and fourth electrodes are separated by about twenty-five millimeters.

13. The method of claim 1, wherein the first and third electrodes are separated by at least about four centimeters.

14. The method of claim 1, wherein the first and third electrodes are separated by at least about ten centimeters.

15. The method of claim 1, further comprising triggering an alarm in response to the pathology assessment.

16. The method of claim 1, further comprising storing the impedance value for later reference.

17. The method of claim 1 further comprising transmitting the impedance value to a monitoring station.

18. The method of claim 1 further comprising injecting a second current between the first and second electrodes, measuring a second potential difference between the third and fourth electrodes, calculating a second impedance value based on the second potential difference and the second current injection, and using the first and second impedance values to assess the pathology near the assessment site, wherein the first and second currents are alternating currents of different frequencies, and wherein the second potential difference results from the second current injected between the first and second electrodes.

19. The method of claim 18, wherein the first current has a frequency of about one kilohertz and the second current has a frequency of about five hundred kilohertz.

20. The method of claim 18 further comprising classifying the pathology based on the first and second impedance values.

21. The method of claim 18, wherein impedance effects of two or more pathologies are discriminated based on the first and second impedance values.

22. The method of claim 1, wherein the current is a composite signal comprising two or more frequencies.

23. The method of claim 22 further comprising extracting frequency components from the potential difference, the frequency components corresponding to the two or more frequencies, wherein the potential difference is a voltage signal.

24. The method of claim 1 further comprising comparing the impedance value to a threshold value.

25. An implantable medical device for measuring impedance for pathology assessment in a living being, comprising:
a pulse generator to inject a current between first and second electrodes implanted in a body of a living being, the first and second electrodes defining a first electric lead field in the body, the first electric lead field oriented between the first and second electrodes;
a voltage measurement circuit to measure a potential difference between third and fourth electrodes implanted in the body, the potential difference resulting from the current injected between the first and second electrodes, the third and fourth electrodes defining a second electric lead field in the body, the second electric lead field oriented between the third and fourth electrodes, wherein the first and second electric lead fields converge near an assessment site within the body, but are substantially separated otherwise; and
a processing unit to calculate an impedance value based on the potential difference and the current injection, and to use the impedance value to assess a pathology near the assessment site.

26. The implantable medical device of claim 25, wherein the assessment site is not within a heart chamber.

27. The implantable medical device of claim 26, wherein the assessment site is a left lung and the pathology is pulmonary edema.

28. The implantable medical device of claim 26, wherein the assessment site is a left ventricular wall of a heart and the pathology is myocardial ischemia.

29. The implantable medical device of claim 25, wherein the second and fourth electrodes are separated by about fifteen millimeters.

30. The implantable medical device of claim 25, wherein the second and fourth electrodes are separated by about twenty-five millimeters.

31. The implantable medical device of claim 25, wherein the first and third electrodes are separated by at least about four centimeters.

32. The implantable medical device of claim 25, wherein the first and third electrodes are separated by at least about ten centimeters.

33. The implantable medical device of claim 25, wherein the processing unit triggers an alarm in response to the pathology assessment.

34. The implantable medical device of claim 25 further comprising a transceiver to transmit the impedance value to a monitoring station.

35. The implantable medical device of claim 25, wherein the pulse generator injects a second current between the first and second electrodes, measures a second potential difference between the third and fourth electrodes, calculates a second impedance value based on the second potential difference and the second current injection, and uses the first and second impedance values to assess the pathology near the assessment site, wherein the first and second currents are alternating currents of different frequencies, and wherein the second potential difference results from the second current injected between the first and second electrodes.

36. A method of measuring impedance phase angle for pathology assessment in a living being, the method comprising:
injecting a current between first and second electrodes implanted in a body of a living being, the first and second electrodes defining a first electric lead field in the body, the first electric lead field oriented between the first and second electrodes;
measuring a potential difference between third and fourth electrodes implanted in the body, the potential difference resulting from the current injected between the first and second electrodes, the third and fourth electrodes defining a second electric lead field in the body, the second electric lead field oriented between the third and fourth electrodes, wherein the first and second electric lead fields converge near an assessment site within the body, but are substantially separated otherwise; and
calculating an impedance phase angle value based on the potential difference and the current injection, and using the impedance phase angle value to assess a pathology near the assessment site.

37. The method of claim 36 further comprising injecting a second current between the first and second electrodes, measuring a second potential difference between the third and fourth electrodes, calculating a second impedance phase angle value based on the second potential difference and the second current injection, and using the first and second impedance phase angle values to assess the pathology near the assessment site, wherein the first and second currents are alternating currents of different frequencies, and wherein the second potential difference results from the second current injected between the first and second electrodes.

38. The method of claim 37 further comprising classifying the pathology based on the first and second impedance phase angle values.

39. The method of claim 37, wherein impedance effects of two or more pathologies are discriminated based on the first and second impedance phase angle values.

* * * * *

UNITED STATES PATENT AND TRADEMARK OFFICE
CERTIFICATE OF CORRECTION

| | | |
|---|---|---|
| PATENT NO. | : 7,447,543 B2 | Page 1 of 1 |
| APPLICATION NO. | : 11/058123 | |
| DATED | : November 4, 2008 | |
| INVENTOR(S) | : Hugo Andres Belalcazar | |

It is certified that error appears in the above-identified patent and that said Letters Patent is hereby corrected as shown below:

Column 22, line 31, in Claim 7, please delete "brachiocepahlic" and insert --brachiocephalic-- therefor.

Signed and Sealed this

Third Day of March, 2009

JOHN DOLL
*Acting Director of the United States Patent and Trademark Office*